(12) United States Patent
Kadyrov et al.

(10) Patent No.: US 7,763,739 B2
(45) Date of Patent: Jul. 27, 2010

(54) CYCLOOLEFIN PHOSPHINE LIGANDS AND THEIR USE IN CATALYSIS

(75) Inventors: Renat Kadyrov, Frankfurt (DE); Juan José Almena Perea, Hanau (DE); Axel Monsees, Frankfurt (DE); Thomas Riermeier, Nidderau-Ostheim (DE); Ilias Ilaldinov, Kazan (RU)

(73) Assignee: Evonik Degussa, GmbH, Essen (DE)

( * ) Notice: Subject to any disclaimer, the term of this patent is extended or adjusted under 35 U.S.C. 154(b) by 769 days.

(21) Appl. No.: 11/579,626

(22) PCT Filed: Apr. 14, 2005

(86) PCT No.: PCT/EP2005/003932

§ 371 (c)(1),
(2), (4) Date: Nov. 6, 2006

(87) PCT Pub. No.: WO2005/108407

PCT Pub. Date: Nov. 17, 2005

(65) Prior Publication Data

US 2008/0306264 A1      Dec. 11, 2008

(30) Foreign Application Priority Data

May 11, 2004   (EP) .................................. 04011152

(51) Int. Cl.
*C07D 333/04* (2006.01)
*C07D 333/02* (2006.01)
(52) U.S. Cl. .............................................. 549/6; 549/5
(58) Field of Classification Search ..................... 549/6, 549/5
See application file for complete search history.

(56) References Cited

U.S. PATENT DOCUMENTS

| 6,284,925 B1 | 9/2001 | Knochel |
| 6,348,620 B1 | 2/2002 | Knochel |
| 6,818,770 B2 | 11/2004 | Selent |
| 2005/0043279 A1 | 2/2005 | Selent |
| 2005/0209455 A1 | 9/2005 | Boerner |
| 2006/0089469 A1 | 4/2006 | Komarov |

FOREIGN PATENT DOCUMENTS

| EP | 04011152.8 | * | 5/2004 |
| WO | WO 96/01831 A | | 1/1996 |
| WO | WO 97/47633 A | | 12/1997 |
| WO | WO 98/22484 A | | 5/1998 |
| WO | WO 99/52915 A | | 10/1999 |
| WO | WO 02/14330 A | | 2/2002 |
| WO | WO 2005/049629 A1 | | 6/2005 |

OTHER PUBLICATIONS

International Search Report for PCT/EP2005/003932 filed Apr. 14, 2005.

Written Opinion of the International Searching Authority for PCT/EP2005/003932 filed Apr. 14, 2005.

International Preliminary Report on Patentability for PCT/EP2005/003932 filed Apr. 14, 2005.

Benincori, Tiziana, et al., "(Diphenylphosphino)-biheteroaryls: the First Example of a New Class of Chiral Atropisomeric Chelating Diphosphine Ligands for Transition Metal Catalysed Stereoselective Reactions," Chem. Commun. 1995, pp. 685-686.

Berens, Ulrich, et al., "Synthesis and Resolution of 2,2'-bis-diphenylphosphino[3,3']biindolyl; a New Atropisomeric Ligand for Transition Metal Catalysis," Tetrahedron: Asymmetry 1996, 7, pp. 285-292.

Bunlaksananusorn, Tanasri, et al., "New P,N Ligands for Asymmetric Ir-Catalyzed Reactions," Angew. Chem. 2003, 115, pp. 4071-4073.

Cullen, William R. and Mangayarkarasy Williams, "The Reaction of . . . Unusual Complexes Formed by Ligand Cleavage Reactions," Canadian J. Chemistry 1980, 58(2), pp. 143-150.

Cullen, William R., et al., "Ditertiary(phosphines and arsines) with perfluoro-(bi-1-cycloalken-1-yl) Bridging Groups. Preparation and Properties Including a Solid State Structure of a Tetracarbonylmolybdenum Derivative," Canadian J. Chemistry 1976, 54(18), pp. 2871-2878.

Gilbertson, Scott R. and Zice Fu, "Chiral P,N-Ligands Based of Ketopinic Acid in the Asymmetric Heck Reaction," Org. Lett. 2001, 3, pp. 161-164.

Gilbertson, Scott R., et al., "Palladium-catalyzed Synthesis of Vinyl Phosphines from Ketones," Tetrahedron Lett. 1999, 40, pp. 8509-8512.

Lotz, Matthias, et al., "Facile Axial Chirality Control by Using a Precursor with Central Chirality. Application to the Preparation of New Axially Chiral Diphosphine Complexes for Asymmetric Catalysis," Chem. Commun. 2002, pp. 2546-2547.

(Continued)

*Primary Examiner*—Charanjit S Aulakh
(74) *Attorney, Agent, or Firm*—Law Office of: Michael A. Sanzo, LLC

(57) ABSTRACT

The present invention concerns novel bidentante optionally N-containing P-ligands of general formula (I)

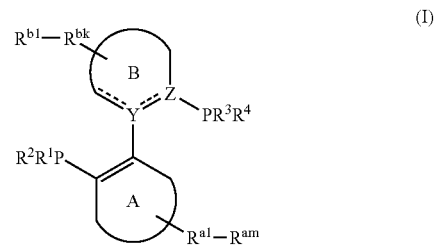

embracing a two-ring-system and processes for synthesizing them, transition metal complexes of these compounds and their use as catalysts.

14 Claims, No Drawings

OTHER PUBLICATIONS

Miyashita, A., et al., "Synthesis of 2,2'-Bis[diphenylphosphino)-1,1'-binapthyl (BINAP), as Atropisometric Chiral Bis(triaryl)phosphine, and Its Use in the Rhodium(I)-Catalyzed Asymmetric Hydrogenation of . . . (Acylamino)acrylic Acids," J. Am. Chem. Soc. 1980, 102, pp. 7932-7934.

Schmid, Rudolf, et al., "Axially Dissymmetric Diphosphines in the Biphenyl Series . . . ," Helv. Chim. Acta 1991, 74, pp. 370-389.

Schmid, Rudolf, et al., "Axially Dissymmetric Bis(triaryl)phosphines in the Biphenyl Series . . . ," Helv. Chim. Acta 1988, 71, pp. 897-929.

Stork, Gilbert and Richard C. A. Isaacs, "Cine Substitution in Vinylstannane Cross-Coupling Reactions," J. Am. Chem. Soc. 1990, 112, pp. 7399-7400.

Svensson, G., et al., "[(+)-(R)-2,2'-Bis(diphenylphosphino)-6,6'-dimethylbiphenyl](8,9,10-trinorborna-2,5-diene)rhodium(I) Tetrafluoroborate," Acta Crystallogr. 1986, pp. 1324-1327.

Wu, Jing, et al., "A New Chiral Dipyridylphosphine Ligand Xyl-P-Phos and its Application in the Ru-catalyzed asymmetric hydrogenation of . . . ketoesters," Tetrahedron Lett. 2002, 43, pp. 1539-1543.

* cited by examiner

CYCLOOLEFIN PHOSPHINE LIGANDS AND THEIR USE IN CATALYSIS

CROSS REFERENCE TO RELATED APPLICATIONS

The present application represents U.S. national stage of international application PCT/EP2005/003932, with an international filing date of Apr. 14, 2005, and which was published in English under PCT Article 21(2) on Nov. 17, 2005. The international application claims priority to European application 04011152.8, filed on May 11, 2004. The contents of this prior application is hereby incorporated by reference in their entirety.

The present invention concerns novel bidentante optionally N-containing P-ligands embracing a two-ring-system and processes for synthesizing them, transition metal complexes of these compounds and their use as catalysts.

BACKGROUND OF THE INVENTION

Transition metal mediated homogeneous catalysis is an indispensable component of modern organic synthesis, rendering a given non-catalytic-process into a truly efficient one. The transition metals are modified by organic ligands to obtain highly selective reactions at higher rates. Especially P and N-containing ligands have been successfully implemented in important organic reactions. The well-designed catalysts serve for carbon-carbon and carbon-heteroatom double bond reduction reactions. Particularly, chiral organic ligands provide a powerful access to a wide variety of enantiomerically pure compounds. The properties of these catalyst are influenced by both the characteristics of the metal and those of the ligands associated with the metal atom. The asymmetry of the metal-catalyzed process is induced, for example, by the chiral ligand scaffold. Therefore, the development of the highly efficient chiral ligands plays a crucial role in expanding the utility of transition metal catalyzed asymmeric reactions. A large and diverse range of ligands have been designed and prepared for use in asymmetric catalysis. The number of novel chiral ligands is growing rapidly. For example, biaryl atropoisomeric ligands have been explored as effective class of a steadily increasing family of axially chiral ligands. Among them, the most well-known example is 2,2'-bis(diphenylphosphino)-1,1'-binaphthyl (BINAP), the synthesis and first application of which was reported by Noyori et al. (A. Miyashita, A. Yasuda, H. Takaya, K. Toriumi, T. Ito, T. Souchi, R. Noyori *J. Am. Chem. Soc.* 1980, 102, 7932). Many variations of the of atropoisomeric biphenyl diphosphines have been reported in the meantime. Substituted in the 6,6'-position 2,2'-bisphosphino-biphenyls are known as BIPHEP-family (G. Svensson, J. Albertsson, T. Frejd, T. Klingstedt *Acta Crystallogr.* 1986, 1324; R. Schmid, M. Cereghetti, B. Heiser, P. Schönholzer, H.-J. Hansen *Helv. Chim. Acta* 1988, 71, 897; R. Schmid, J. Foricher, M. Cereghetti, P. Schönholzer *Helv. Chim. Acta* 1991, 74, 370.) The working-group of Zhang has described TunaPhos with tuneable dihedral angles by introducing a bridge with variable length to link the chiral atropoisomeric biaryl groups (S. Wu, W. Wang, W. Tang, M. Lin, X. Zhang *Org. Lett.* 2002,).

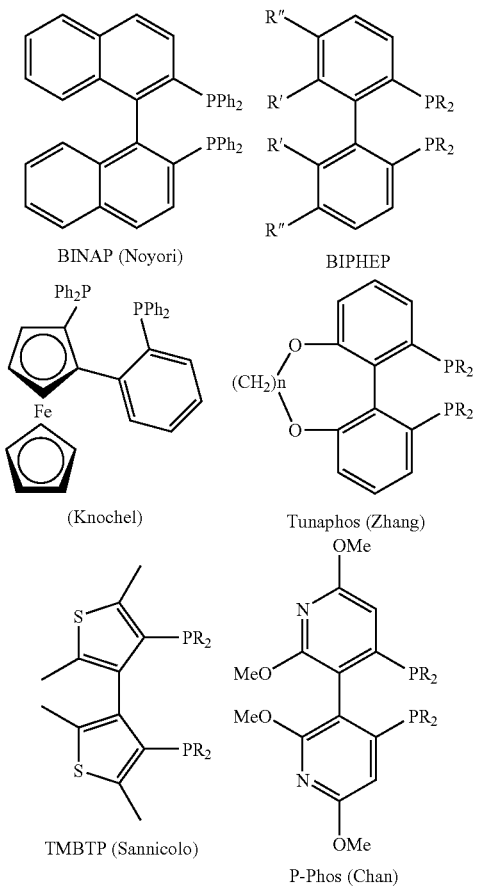

BINAP (Noyori)

BIPHEP (Knochel)

Tunaphos (Zhang)

TMBTP (Sannicolo)

P-Phos (Chan)

Sannicolo et al. have reported the first example of a diphosphine ligand TMBPT, where the biarylic system was replaced by a bi-heteroarylic system (T. Benincori, E. Brenna, F. Sannicolo, L. Trimarco, P. Antognazza, E. Cesarotti *Chem. Commun.* 1995, 685). In designing this ligand, it was to achieve to compare the novel geometry of the interconnected five-membered rings with well-known biphenylic systems. A further example of a diphosphine ligand containing a dipyridyl backbone is P-Phos which was prepared by Chan et al. (J. Wu, W. H. Kwok, K. H. Lam, Z. Y. Zhou, C. H. Yeung, A. S. C. Chan *Tetrahedron Lett.* 2002, 43, 1539-1543). Knochel et al. introduced new types of ferrocene ligands (M. Lotz, G. Kramer, P. Knochel *Chem. Commun.*, 2002, 2546-2547)

Recently, Gilbertson et al. have reported that vinyl phosphines are readily accessible through ketones by palladium-catalyzed coupling of the corresponding vinyl triflate with diphenylphosphine (S. R. Gilbertson, Z. Fu, G. W. Starkey *Tetrahedron Lett.* 1999, 40, 8509-8512). The group has developed novel chiral P,N-ligands starting from commercial available (1S)-(+)-ketopinic acid (S. R. Gilbertson, Z. Fu *Org. Lett.* 2001, 3, 161-164). The known camphor enol triflate undergo facile coupling with arylzinc reagents to afford arylbornene (G. Stork, R. C. A. Isaacs *J. Am. Chem. Soc.* 1990, 112, 7399-7400). Knochel et al. used this method for the preparation of new P,N-ligands from readily available chiral building blocks such as (R)-camphor and (R)-nopinone. (T. Bunlaksananusorn, K. Polbern, P. Knochel *Angew. Chem.* 2003, 115, 4071-4073)

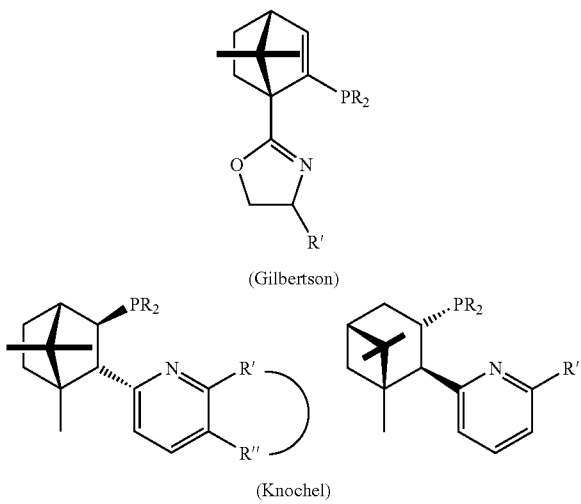

(Gilbertson)

(Knochel)

SUMMARY OF THE INVENTION

It is an object of the present invention to provide novel bidentate phosphorus ligand systems. The basic framework of the compounds of the invention in each case comprises a cycloolefinic or heterocycloolefinic ring system connected to a carbocyclic or heterocyclic system via a direct carbon-carbon or carbon-nitrogen single bond.

A second aspect of the present invention relates to the easy way of preparing the ligands of the invention starting from e.g. natural products like camphor. Via well established coupling techniques the ligands of the invention are obtained in a simple manner.

A further aspect of the invention is directed to special transition metal catalysts embracing a ligand system according to the invention.

Still another embodiment of the invention deals with using said catalysts in organic chemical reactions to produce, in particular, highly enantiomerically enriched organic compounds if suitable chiral catalysts are used.

DEFINITIONS

For convenience, before further description of the present invention, certain terms employed in the specification, examples, and appended claims are collected here.

The term "room temperature" is recognized in the art and means a comfortable indoor temperature, generally between 15 and 25 C.

The term "catalytic amount" is recognized in the art and means a substoichiometric amount of a reagent (a catalyst) relative to the limiting reagent(s). The term "meso compound" is recognized in the art and means a chemical compound which has at least two chiral centers but is achiral due to the presence of an internal plane or point of symmetry.

The term "chiral" refers to molecules which have the property of non-superimposability of their mirror image partner, while the term "achiral" refers to molecules which are superimposable on their mirror image partner. A "prochiral molecule" is a molecule which has the potential to be converted to a chiral molecule in a particular process. The term "stereoisomers" refers to compounds which have identical chemical constitution, but differ with regard to the arrangement of the atoms or groups in space. In particular, "enantiomers" refer to two stereoisomers of a compound which are non-superimposable mirror images of one another. "Diastereomers", on the other hand, refers to stereoisomers with two or more centers of dissymmetry and whose molecules are not mirror images of one another. "Racemic mixture" is an equimolar mixture of a pair of enantiomers that is, therefore, optically inactive. Furthermore, a "stereoselective process" is one which produces a particular stereoisomer of a reaction product in preference to other possible stereoisomers of that product. An "enantioselective process" is one which favors production of one of the two possible enantiomers of a reaction product. The subject method is said to produce a "stereoisomerically-enriched" product (e.g., enantiomerically-enriched or diastereomerically-enriched) when the yield of a particular stereoisomer of the product is greater by a statistically significant amount relative to the yield of that stereoisomer resulting from the same reaction run in the absence of a chiral catalyst. For example, a reaction which routinely produces a racemic mixture will, when catalyzed by one of the subject chiral catalysts, yield an e.e. for a particular enantiomer of the product. The term "regioisomers" refers to compounds which have the same molecular formula but differ in the connectivity of the atoms. Accordingly, a "regioselective process" is one which favors the production of a particular regioisomer over others, e.g., the reaction produces a statistically significant majority of a certain regioisomer. As discussed more fully below, the reactions contemplated in the present invention include reactions which are enantioselective, diastereoselective, and/or regioselective. An enantioselective reaction is a reaction which converts an achiral reactant to a chiral product enriched in one enantiomer. Enantioselectivity is generally quantified as "enantiomeric excess" (ee) defined as follows:

% enantiomeric excess $A$ (ee)=(% enantiomer $A$)−(% enantiomer $B$)

where A and B are the enantiomers formed. Additional terms that are used in conjunction with enatioselectivity include, "optical purity" or "optical activity". An enantioselective reaction yields a product with an e.e. greater than zero. Preferred enantioselective reactions yield a product with an e.e. greater than 20%, more preferably greater than 50%, even more preferably greater than 70%, and most preferably greater than 80%. A diastereoselective reaction converts a reactant or reactants (which may be achiral, racemic, non-racemic or enantiomerically pure) to a product enriched in one diastereomer.

The term "non-racemic" or "enantiomerically enriched" means a preparation having greater than 50% of a desired stereoisomer, more preferably at least 75%. Substantially non-racemic" refers to preparations which have greater than 90% ee for a desired stereoisomer, more preferably greater than 95% ee.

The term "alkyl" refers to the radical of saturated aliphatic groups, including straightchain alkyl groups, branched-chain alkyl groups, such as methyl, ethyl, n-propyl, isopropyl, n-butyl, isobutyl, t-butyl, octyl, decyl, and the like. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer. Moreover, the term "alkyl" (or "lower alkyl") as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a nitro, an azide, a halogen, a hydroxyl, a thiol, a nitril, a (thio)isocyanate, an alkoxyl, an aryloxyl, an alkylthio, an arylthio, a disulfide, an amine, an ammonium cation, a hydrazine, a hydrazide, a selenoalkyl, a (thio)carbonyl (such as a (thio)ketone, a (thio)acyl or a (thio)formyl), an imine, an oxyme, a hydrazone, an azo group, a (thio)carboxylic acid or ester, a thiolcarboxylic acid or thiolester, a thiono ester, a (thio)amide, an imidate, an amidine, a (thio)carboxylate (including (thio)formate), a (thio)acylamine, a (thio)carbonate, a (thio)carbamate, a (thio)urea, a carbodimide, a sulfoxyde, a sulfone, a sulfonate, a sulfonamide, a sulfonic acid or ester, a sulfinic acid or ester, a sulfamoyl, a sulfate, a (thio)phosphoryl (including phosphonic and phosphinic acid), an oxyphosphoryl (including thiolphosphoryl, oxythiophosphoryl, dithiophosphoryl and phosphoric acid), a phosphorane, a phosphonium cation, a silyl, a silyloxy, a borono, a (dithio)ketal (including (dithio)acetal), an ortho ester, an amidacetal, a borane, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl and oxyphosphoryl, sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. The term "aralkyl", as used herein, refers to an alkyl group substituted with an aryl group (e.g., an aromatic or heteroaromatic group).

The term "alkyl" as used herein includes the term "cycloalkyl", which refers to an aliphatic cyclic moiety, such as cyclopentyl, cyclohexyl, cyclooctyl, and the like. Cycloalkyl (alicyclic) groups may be bicyclic or polycyclic, such as norbornyl, adamantyl, and the like. The cycloalkyl group can be substituted at one or more ring positions with such substituents as described above for the alkyls. Preferred cycloalkyls have from 3-20 carbon atoms in their ring structure, and more preferably have from 4 to 12 carbons in the ring structure.

The terms "alkenyl", "cycloalkenyl", and "alkynyl" refer to unsaturated aliphatic and alicyclic groups analogous in length and possible substitution to the alkyls described above, but that contain at least one double or triple bond respectively, such as ethenyl, n-propenyl, isopropenyl, n-butenyl, isobutenyl, octenyl, decenyl, tetradecenyl, hexadecenyl, eicosenyl, tetracosenyl, cyclobutenyl, cyclohexenyl, cyclohexadienyl, norbornadienyl, ethynyl, n-propynyl, and the like.

Unless the number of carbons is otherwise specified, "lower alkyl" as used herein means an alkyl group, as defined above, but having from 1 to 10 carbons, more preferably from 1 to 6 carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aryl" as used herein includes 5-, 6- and 7-membered single-ring aromatic groups that may include from 0 to 4 heteroatoms, for example benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, amino, ammono, nitro, thiol, imino, amido, phosphoryl, oxyphosphoryl, phosphonium, borono, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "substituted aryl" as used herein, and unless otherwise specified, also includes π-komplexes of aromatic rings with transition metals like ferrocene and chromtricarbonylbenzene. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls, such as indenyl, naphthyl, indolyl, and the like.

The terms "heterocyclyl" or "heterocyclic group" refer to 3- to 10-membered ring structures, more preferably 3- to 7-membered rings, whose ring structures include from 1 to 4 heteroatoms. Heterocycles can also be polycycles. Heterocyclyl groups include, for example, thiophene, thianthrene, tetrahydrofuran, pyran, isobenzofuran, chromene, xanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, alkoxy, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulkydryl, imino, amido, phosphoryl, oxyphosphoryl, carboxyl, silyl, alkoxy, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or non-aromatic ring in which each atom of the ring is carbon.

The term "heteroatom" as used herein means an atom of any element other than carbon or hydrogen. Preferred heteroatoms are nitrogen, oxygen, sulfur, phosphorous and silicon.

As used herein, the term "nitro" means —$NO_2$; the term "azide" means —$N_3$; the term "halogen" designates —F, —Cl, —Br or —I; the term "thiol" means —SH; the term "hydroxyl" means —OH; the terms "cyano" and "nitril" mean —CN; the term "isocyanate" means —N=C=O; the term "thioisocyanate" means —N=C=S; and the term "sulfonyl" means —$SO_2$—.

The terms "alkoxyl" or "alkoxy" as used herein refers to an alkyl, an alkenyl, an alkynyl, a cycloalkyl, a cycloalkenyl, a heterocyclic group as defined above, having an oxygen radical attached thereto. Representative alkoxyl groups include methoxy, ethoxy, propyloxy, tert-butoxy and the like.

The term "aryloxyl" as used herein refers to an aryl or an heteroaryl, as defined above, having an oxygen radical attached thereto. Representative aryloxyl groups include phenoxy, and the like.

The term "alkylthio" refers to an alkyl, an alkenyl, an alkynyl, a cycloalkyl, a cycloalkenyl, a heterocycle group as defined above, having a sulfur radical attached thereto.

In preferred embodiments, the "alkylthio" moiety is represented by one of —S-alkyl, —S-alkenyl and —S-alkynyl. Representative alkylthio groups include methylthio, ethyl thio, and the like.

The term "arylthio" as used herein refers to an aryl or an heteroaryl, as defined above, having an sulfur radical attached thereto. Representative arylthio groups include phenylthio, and the like.

The term "disulfide" is recognized in the art and refers to both unsubstituted and substituted disulfides, e.g., a moiety that can be represented by the general formula:

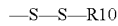

wherein R10 represents a hydrogen, an alkyl, an alkenyl, an alkynyl, an aryl, an heteroaryl, cycloalkyl, a cycloalkenyl, a heterocycle or a polycycle.

The terms "amine" and "amino" are art recognized and refer to both unsubstituted and substituted amines, e.g., a moiety that can be represented by the general formula:

wherein R10 and R11 each independently represent a hydrogen, an alkyl, an alkenyl, an alkynyl, an aryl, an heteroaryl, cycloalkyl, a cycloalkenyl, a heterocycle or a polycycle, and R10 may be selected from one of hydroxy, alkoxy and aryloxy, or R10 and R11 taken together with the N atom to which they are attached complete a heterocycle having from 4 to 8 atoms in the ring structure; the term "alkylamine" as used herein means an amine group, as defined above, having a substituted or unsubstituted alkyl attached thereto, i.e., at least one of R10 and R11 is an alkyl group.

The term "ammonium cation" is art recognized and refers to both unsubstituted and substituted ammonium groups, e.g., a moiety that can be represented by the general formula:

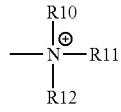

wherein R10, R11 and R12 each independently represent a hydrogen, an alkyl, an alkenyl, an alkynyl, an aryl, an heteroaryl, cycloalkyl, a cycloalkenyl, a heterocycle or a polycycle, and any two or three of substituents from R10, R11 and R12 taken together with the N atom to which they are attached complete a heterocycle or bicycling ring having from 4 to 12 atoms in the ring structure.

The term "hydrazine" is art recognized and refers to both unsubstituted and substituted hydrazines, e.g., a moiety that can be represented by the general formula:

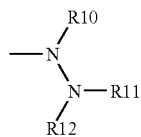

wherein R10, R11 and R12 each independently represent a hydrogen, an alkyl, an alkenyl, an alkynyl, an aryl, an heteroaryl, cycloalkyl, a cycloalkenyl, a heterocycle or a polycycle, or any two of substituents from R10, R11 and R12 taken together complete a heterocycle having from 4 to 8 atoms in the ring structure. Particularly, if one of substituent R10, R11, R12 is selected from the acyl —C(O)R, thioacyl —C(S)R, sulfoxyde, sulfone or phosphoryl group, the above formula represents a "hydrazide" group.

The term "(thio)carbonyl" is art recognized and includes such moieties as can be represented by the general formula:

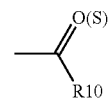

wherein R10 represents a hydrogen, an alkyl, an alkenyl, an alkynyl, a cycloalkyl, a cycloalkenyl, a heterocycle, an aryl, an heteroaryl group or carbonyl or thiocarbonyl group as defined above. Particularly, if R10 is not hydrogen, the above formula represents a "ketone" or a "thioketone" group. Where R10 is hydrogen, the above formula represents an "aldehyde" group. The above defined group is known also as "acyl" group, particularly when R10 is hydrogen, the above formula represents an "formyl" group.

The term "imine" is art recognized and refers to both unsubstituted and substituted imines, e.g., a moiety that can be represented by the general formula:

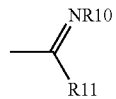

wherein R10 and R11 each independently represent a hydrogen, an alkyl, an alkenyl, an alkynyl, an aryl, an heteroaryl, cycloalkyl, a cycloalkenyl, a heterocycle or a polycycle, or R10 and R11 taken together complete a heterocycle having from 4 to 8 atoms in the ring structure. Also R10 may represent an acyl —C(O)R, a thioacyl —C(S)R, a sulfoxyde, a sulfone or a phosphoryl group. Where R10 is hydroxy, an alkoxy or an aryloxy, the formula represents an "oxyme". Where R10 is aminogroup, the formula represents a "hydrazone". Where R10 is —N=CR'R, the above formula represents an "azo" group.

The terms "(thio)carboxylic acid" and "(thio)carboxylic ester" are art recognized and include a moiety that can be represented by the general formula:

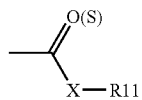

where X is an oxygen or sulfur, and R11 is an alkyl, an alkenyl, an alkynyl, a cycloalkyl, a cycloalkenyl, a heterocycle, an aryl or an heteroaryl group as defined above, the moiety is referred to herein as a "carboxylic ester", and particularly when R11 is a hydrogen, the formula represents a "carboxylic acid". The term "carboxylic acid" as used herein intends also carboxylic acid salts where R11 is an mono- or polyvalent cation. Where X is a sulfur and R11 is not hydrogen, the formula represents a "thiolester". Where X is a sulfur and R11 is hydrogen, the formula represents a "thiolcarboxylic acid". In general, where the oxygen atom of the above formula is replaced by sulfur, the formula represents a "thiono esters".

The terms "amide" and "thioamide" are art recognized as an amino-substituted carbonyl or thiocarbonyl and include moieties that can be represented by the general formula:

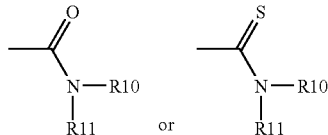

wherein R10 and R11 each independently represent a hydrogen, an alkyl, an alkenyl, an alkynyl, an aryl, an heteroaryl, cycloalkyl, a cycloalkenyl, a heterocycle or a polycycle, and R10 may represent a hydroxy, an alkoxy, an aryloxy. Where R10 is one of defined above carbonyl or thiocarbonyl group, the formula represent "imide" group. R10 and R11 taken together with the N atom to which they are attached may complete a heterocycle having from 4 to 8 atoms in the ring structure.

The term "imidate" is art recognized as an imino-substituted carboxylic acid or ester and include a moiety that can be represented by the general formula:

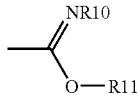

wherein R10 and R11 each independently represent a hydrogen, an alkyl, an alkenyl, an alkynyl, an aryl, an heteroaryl, cycloalkyl, a cycloalkenyl, a heterocycle or a polycycle, and R10 may represent one of carbonyl or thiocarbonyl group. Particularly if R10 is hydroxy, an alkoxy or an aryloxy, the formula represents a "hydroxamic acid" or "hydroxamic ester".

The term "amidine" is art recognized as an imino-substituted amide and include a moiety that can be represented by the general formula:

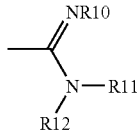

wherein R10, R11 and R12 each independently represent a hydrogen, an alkyl, an alkenyl, an alkynyl, an aryl, an heteroaryl, cycloalkyl, a cycloalkenyl, a heterocycle or a polycycle, or any two of substituents from R10, R11 and R12 taken together complete a heterocycle having from 4 to 8 atoms in the ring structure. Also R10 may represent an acyl —C(O)R, a thioacyl —C(S)R, a sulfoxyde, a sulfone or a phosphoryl group.

The term "(thio)carboxylate" is art recognized and includes a moiety that can be represented by the general formula:

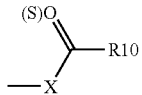

wherein R10 represents a hydrogen, an alkyl, an alkenyl, an alkynyl, a cycloalkyl, a cycloalkenyl, a heterocycle, an aryl or an heteroaryl group as defined above. Particularly, if X is an oxygen and R10 is hydrogen, the formula represents a "formate".

The terms "acylamine" and "thioacylamine" are art-recognized and refer to a moieties that can be represented by the general formula:

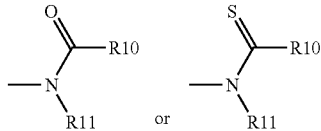

wherein R10 and R11 each independently represent a hydrogen, an alkyl, an alkenyl, an alkynyl, an aryl, an heteroaryl, cycloalkyl, a cycloalkenyl, a heterocycle or a polycycle. Where R11 is one of defined above carbonyl or thiocarbonyl group, the formula represent "imido" group. R10 and R11 taken together with the N atom to which they are attached may complete a heterocycle having from 4 to 8 atoms in the ring structure.

The term "carbonate" as used herein refers to —OC(O)OR group; "thiocarbonate" —OC(S)OR group, "carbamate" as used herein refers to —OC(O)NR'R or —NR'C(O)OR group; "thiocarbamate" as used herein refers to —OC(S)NR'R or —NR'C(S)OR group; "urea" as used herein refers to —NRC(O)NR'R" group; "thiourea" as used herein refers to —NRC(S)NR'R" group; "carbodiimide" as used herein refers to —N═C═NR group.

The term "guanidine" is art recognized and includes a moiety that can be represented by the general formula:

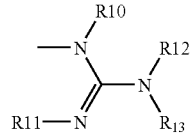

wherein R10, R11, R12 and R13 each independently represent a hydrogen, an alkyl, an alkenyl, an alkynyl, an aryl, an heteroaryl, cycloalkyl, a cycloalkenyl, a heterocycle or a polycycle, or any two of substituents from R10, R11, R12 and R13 taken together complete a heterocycle having from 4 to 8 atoms in the ring structure. R10, R11 or/and R12 can also be selected from a group consisting of acyl —C(O)R, thioacyl —C(S)R, sulfoxyde, sulfone or phosphoryl group.

The term "sulfoxide" is art recognized and includes a moiety that can be represented by the general formula:

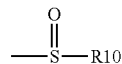

in which R10 represents a hydrogen, an alkyl, an alkenyl, an alkynyl, an aryl, an heteroaryl, cycloalkyl, a cycloalkenyl, a heterocycle or a polycycle.

The term "sulfone" is art recognized and includes a moiety that can be represented by the general formula:

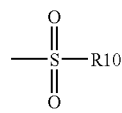

in which R10 represents a hydrogen, an alkyl, an alkenyl, an alkynyl, an aryl, an heteroaryl, cycloalkyl, a cycloalkenyl, a heterocycle or a polycycle. The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively.

The term "sulfonate" is art recognized and includes a moiety that can be represented by the general formula:

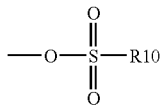

in which R10 represents a hydrogen, an alkyl, an alkenyl, an alkynyl, an aryl, an heteroaryl, cycloalkyl, a cycloalkenyl, a heterocycle or a polycycle. The terms triflate, tosylate, mesylate, and nonaflate are art-recognized and refer to trifluoromethanesulfonate, p-toluenesulfonate, methanesulfonate, and nonafluorobutanesulfonate functional groups and molecules that contain said groups, respectively.

The term "sulfonamide" is art recognized and includes a moiety that can be represented by the general formula:

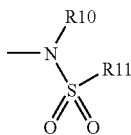

in which R10 and R11 are as defined above.

The terms "sulfonic acid" and "sulfonic acid esters" are art recognized and includes a moiety that can be represented by the general formula:

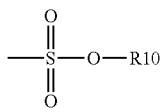

in which R10 represents a hydrogen, an alkyl, an alkenyl, an alkynyl, an aryl, an heteroaryl, cycloalkyl, a cycloalkenyl, a heterocycle or a polycycle. Particularly when R10 is a hydrogen, the formula represents a "sulfonic acid". The term "sulfonic acid" as used herein intends also sulfonic acid salts where R10 is an mono- or polyvalent cation.

The term "sulfamoyl" is art-recognized and includes a moiety that can be represented by the general formula:

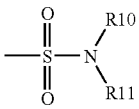

in which R10 and R11 are as defined above.

The terms "sulfinic acid" and "sulfinic acid esters" are art recognized and includes a moiety that can be represented by the general formula:

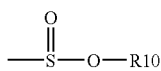

in which R10 represents a hydrogen, an alkyl, an alkenyl, an alkynyl, an aryl, an heteroaryl, cycloalkyl, a cycloalkenyl, a heterocycle or a polycycle. Particularly, when R10 is a hydrogen, the formula represents a "sulfinic acid". The term "sulfinic acid" as used herein intends also sulfonic acid salts where R10 is an mono- or polyvalent cation.

The term "sulfate" is art recognized and includes a moiety that can be represented by the general formula:

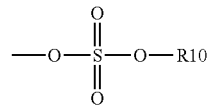

in which R10 is as defined above.

A "phosphoryl" or "thiophosphoryl" can in general be represented by the formula:

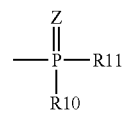

wherein Z represented S or O, and R10 and R11 each independently represent a hydrogen, an alkyl, an alkenyl, an alkynyl, an aryl, an heteroaryl, cycloalkyl, a cycloalkenyl, a heterocycle, hydroxy, alkoxy, aryloxy, silyloxy, thiol, alkylthio, arylthio, amino, hydrazine, nitril, an R10 and R11 taken together with the P atom to which they are attached complete a heterocycle having from 4 to 8 atoms in the ring structure. R10 can also be selected from a group consisting of acyl, thioacyl, imine, (thio)carboxylic acid or ester, (thio)amide, (thio)carboxylate, (thio)acylamine, (thio)carbonate, (thio)carbamate, (thio)urea, oxyphosphoryl, thiolphosphoryl or oxythiophosphoryl. Particularly, when R10 is an alkyl, an alkenyl, an alkynyl, an aryl, an heteroaryl, cycloalkyl, a cycloalkenyl, and R11 is hydroxy, the formula represents a "phosphinic acid". The term "phosphinic acid" as used herein intends also phosphinic acid salts. When R10 and R11 are hydroxy groups, the formula represents a "phosphonic acid". The term "phosphonic acid" as used herein intends also phosphonic acid salts.

A "oxyphosphoryl", "thiolphosphoryl", "oxythiophosphoryl" or "dithiophosphoryl" can in general be represented by the formula:

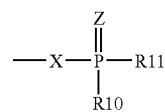

wherein X and Z represented S or O, R10 and R11 are as defined above. Particularly, when R10 is hydrogen and R11 is hydroxy, the formula represents a "hypophosphorous acid". The term "hypophosphorous acid" as used herein intends also hypophosphorous acid salts. When R10 and R11 are hydroxy groups, the formula represents a "phosphoric acid". The term "phosphoric acid" as used herein intends also phosphoric acid salts.

The term "phosphorane", as used herein, refers to a moiety that can be represented by the general formula:

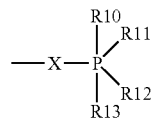

Wherein X is the bond or represents an oxygen, sulfur or the —NR-group, and R10, R11, R12 and R13 each independently represent a hydrogen, an alkyl, an alkenyl, an alkynyl, an aryl, an heteroaryl, cycloalkyl, a cycloalkenyl, a heterocycle, alkoxy, aryloxy, silyloxy, alkylthio, arylthio, amino, and any two or three of substituents from R10, R11, R12 and R13 taken together with the P atom to which they are attached complete a heterocycle or bicycling ring having from 4 to 12 atoms in the ring structure.

The term "phosphonium cation" is art recognized and includes a moiety that can be represented by the general formula:

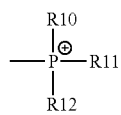

wherein R10, R11 and R12 each independently represent a hydrogen, an alkyl, an alkenyl, an alkynyl, an aryl, an heteroaryl, cycloalkyl, a cycloalkenyl, a heterocycle or a polycycle, and any two or three of substituents from R10, R11 and R12 taken together with the P atom to which they are attached complete a heterocycle or bicycling ring having from 4 to 12 atoms in the ring structure.

A "selenoalkyl" refers to an alkyl group having a substituted seleno group attached thereto. A "selenoaryl" refers to an aryl group having a substituted seleno group attached thereto.

The term "silyl" is art recognized and refers to both unsubstituted and substituted silanes, e.g., a moiety that can be represented by the general formula:

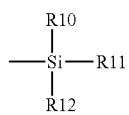

wherein R10, R11 and R12 each independently represent a hydrogen, an halogen, an alkyl, an alkenyl, an alkynyl, an aryl, an heteroaryl, cycloalkyl, a cycloalkenyl, a heterocycle or a polycycle, an alkoxy, an alkylthio, an aryloxy, an arylthio, or a further silyl group, and any two or three of substituents from R10, R11 and R12 taken together with the Si atom to which they are attached complete a heterocycle or bicycling ring having from 4 to 12 atoms in the ring structure.

The terms "silyloxyl" as used herein refers to a silyl having an oxygen radical attached thereto.

The term "borono", as used herein, refers to a moiety that can be represented by the general formula:

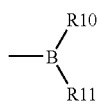

Wherein R10 and R11 each independently represent hydroxy, alkoxy, aryloxy, silyloxy, alkylthio, arylthio, amino, and R10, R11 taken together with the B atom to which they are attached complete a heterocycle having from 4 to 12 atoms in the ring structure.

The terms "ketal" and "dithioketal", as used herein, refer to a moiety that can be represented by the general formula:

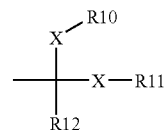

Where X is an oxygen or sulfur, R10 and R11 each independently represent an alkyl, an alkenyl, an alkynyl, an aryl, an heteroaryl, cycloalkyl, a cycloalkenyl, a heterocycle, and R10, R11 taken together complete a heterocycle having from 4 to 12 atoms in the ring structure. R12 represents a hydrogen, an halogen, an alkyl, an alkenyl, an alkynyl, an aryl, an heteroaryl, cycloalkyl, a cycloalkenyl, a heterocycle or a polycycle. Particularly, when R12 is hydrogen, the formula represents a "acetal". When R12 is an alkoxy, aryloxy, silyloxy, alkylthio or arylthio group, the formula represents a "ortho ester". When R12 is an amino group, the formula represents a "amidacetal".

The phrase "protecting group" as used herein means temporary modifications of a potentially reactive functional group which protect it from undesired chemical transformations. Examples of such protecting groups include esters of carboxylic acids, silyl ethers of alcohols, and acetals and ketals of aldehydes and ketones, respectively. The field of protecting group chemistry has been reviewed (T. W. Greene, P. G. M. Wuts *Protective Groups in Organic Synthesis,* 3rd ed.; John Wiley & Sons, Inc.: New York, 1999).

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. Illustrative substituents include, for example, those described above. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

For purposes of this invention, the chemical elements are identified in accordance with the Periodic Table of the Elements, CAS version, Handbook of Chemistry and Physics, 78$^{th}$ Ed., 1997-1998, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and non-aromatic organic compounds which can be substituted or unsubstituted.

The structures shown refer to all the possible diastereomers and enantiomers and their mixtures that are possible. The structures also embrace all salts being obtainable from structures of the invention by reaction with optionally strong acids or optionally strong bases. Strong in this respect is understood as having a pKs or pKb, respectively, of <5 or <3 more preferably <2 or <1.5.

DETAILED DESCRIPTION OF THE INVENTION

In one aspect of the invention, novel ligands for metals, preferably transition metals, are provided. The subject ligands are represented by general structure (I),

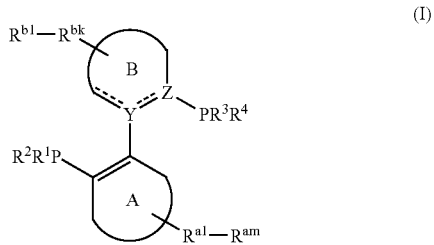

wherein
= represents an optional double bond;
Y is the group selected from CR, =C and N; whereby R is the same like $R^{b1}$;
Z is the group selected from CR, =C, and N; whereby R is the same like $R^{a1}$;
A represents a ring structure selected from a group consisting of monocyclic or polycyclic carbo- or heterocyclic partially saturated non-aromatic rings, said rings comprising from 5 to 8 atoms;
B represents a ring structure selected from a group consisting of monocyclic or polycyclic saturated or partially saturated carbocyclic or heterocyclic, aromatic or heteroaromatic rings, said rings comprising from 4 to 8 atoms in a ring structure;
A and B independently may be unsubstituted or substituted with $R^{a1}$-$R^{am}$ and $R^{b1}$-$R^{bk}$, respectively, any number m and k of times up to the limitations imposed by stability and the rules of valence being possible;
$R^{a1}$-$R^{am}$ and $R^{b1}$-$R^{bk}$ for each occurrence, independently represent hydrogen, halogen, nitril, alkyl, aralkyl, alkenyl, alkynyl, cycloalkyl, polycyclyl, heterocyclyl, an aromatic or heteroaromatic moiety, nitro, azide, (thio)isocyanate, hydroxyl, alkoxyl, aryloxyl, thiol, alkylthio, arylthio, disulfide, amine, ammonium cation, hydrazine, hydrazide, selenoalkyl, (thio)carbonyl (such as a (thio)ketone, a (thio) acyl or a (thio)formyl), imine, oxyme, hydrazone, azo group, (thio)carboxylic acid and (thio)carboxylic ester, thiolcarboxylic acid or thiolester, thiono ester, (thio)amide, imidate, amidine, (thio)carboxylate (including (thio)formate), (thio)acylamine, (thio)carbonate, (thio)carbamate, (thio)urea, carbodimide, anhydride, sulfoxyde, sulfone, sulfonate, sulfonamide, sulfonic acid or ester, sulfinic acid or ester, sulfamoyl, sulfate, (thio)phosphoryl (including phosphonic and phosphinic acid), oxyphosphoryl (including thiolphosphoryl, oxythiophosphoryl, dithiophosphoryl and phosphoric acid), phosphorane, phosphonium cation, silyl, silyloxy, borono, (dithio)ketal (including (dithio)acetal), ortho ester, amidacetal, amine oxide, aziridine, epoxide;
any pair(s) of substituents, selected from the group consisting of $R^{a1}$-$R^{am}$ or $R^{b1}$-$R^{bk}$, taken together may represent a ring selected from a group consisting of monocyclic or polycyclic saturated or partially saturated carbocyclic or heterocyclic, aromatic or heteroaromatic rings, said rings comprising from 4 to 8 atoms and may comprise from 0 to 3 heteroatoms;
$R^1$, $R^2$, $R^3$ and $R^4$ for each occurrence, independently represent alkyl, aryl, aralkyl, alkenyl, alkynyl, alkoxyl, aryloxyl, alkylthio, arylthio, unsubstituted or substituted cyclic moiety, selected from a group consisting of monocyclic or polycyclic saturated or partially saturated carbocyclic or heterocyclic, aromatic or heteroaromatic rings said rings comprising from 4 to 8 atoms and may comprise from 0 to 3 heteroatoms;
$R^1$ and $R^2$, and/or $R^3$ and $R^4$, taken together may represent a ring selected from a group consisting of unsubstituted or substituted cyclic moiety, selected from a group consisting of monocyclic or polycyclic saturated or partially saturated carbocyclic or heterocyclic, aromatic or heteroaromatic rings said rings comprising from 3 to 8 atoms;
and the ligand, when chiral, may be provided in the form of a mixture of enantiomers or as a single enantiomer.

Mentioned ligands are highly versatile tools for metal catalysed organic reactions. High chiral induction and acceleration of the underlying chemical reaction can be born by applying these compounds. An important advantage of the invitation however is the possible creation of highly asymmetric environments around the metal centre by these ligand systems. The new ligand systems combine the features of effective asymmetric induction with independently easily modifiable organophosphorus donors, which can be modified over an extraordinarily wide range in a simple fashion in terms of their steric and electronic properties.

The ligand of claim 1, wherein $R^1$ is not equal to $R^2$, the P attached to the ring A is asymmetric and the compound is enriched in one enantiomer or diastereomer when other chiral element(s) is(are) present in the structure (I) and/or $R^3$ is not equal to $R^4$, the P attached to the ring B is asymmetric and the compound is enriched in one enantiomer or diastereomer when other chiral element(s) is(are) present in the structure (I).

In preferred embodiments, the subject ligands are represented by general structure (Ia)

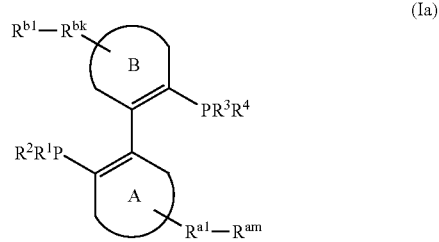

wherein A and B and residues $R^1$-$R^4$, $R^{a1}$-$R^{am}$ and $R^{b1}$-$R^{bk}$ remain the same as mentioned above.

Preferred embodiments are those mentioned above for formula (I).

In certain embodiments, the ligands are represented by general structure (Ia) and the associated definitions, when A is equal to B the compound is C2 symmetric.

In particularly preferred embodiments, the ligands are represented by general structure (Ia) and the associated definitions, wherein
$R^1$, $R^2$, $R^3$ and $R^4$ for each occurrence, independently represent alkyl, alkenyl, alkynyl, alkoxyl, aryloxy, amino, alkylthio, arylthio, heteroalkyl and/or unsubstituted or substituted cyclic moiety, selected from a group consisting of monocyclic or polycyclic saturated or partially saturated carbocyclic or heterocyclic, aromatic or heteroaromatic rings said rings comprising from 4 to 8 atoms in a ring structure and said ring may bear additional substituents or be unsubstituted;

$R^1$ and $R^2$, and/or $R^3$ and $R^4$, taken together may represent a ring selected from a group consisting of monocyclic or polycyclic saturated or partially saturated carbocyclic or heterocyclic, aromatic or heteroaromatic rings said rings comprising from 3 to 8 atoms in the backbone and said ring may bear additional substituents or be unsubstituted;

and the ligand, when chiral, may be provided in the form of a mixture of enantiomers or as a single enantiomer.

Particularly preferred ligands, without limitation, are depicted in FIG. 1.

FIG. 1:

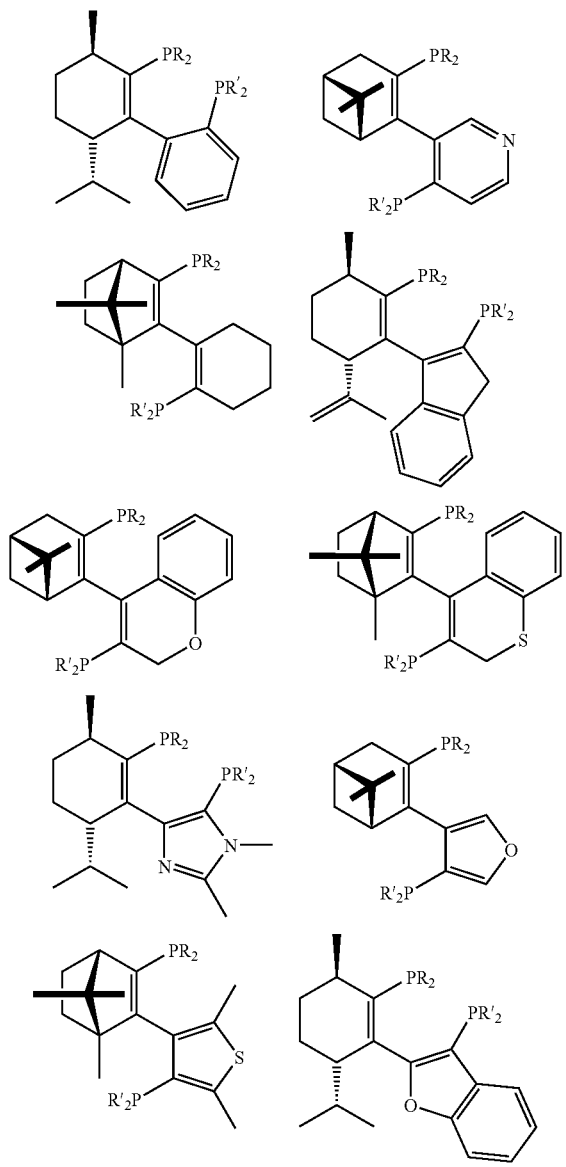

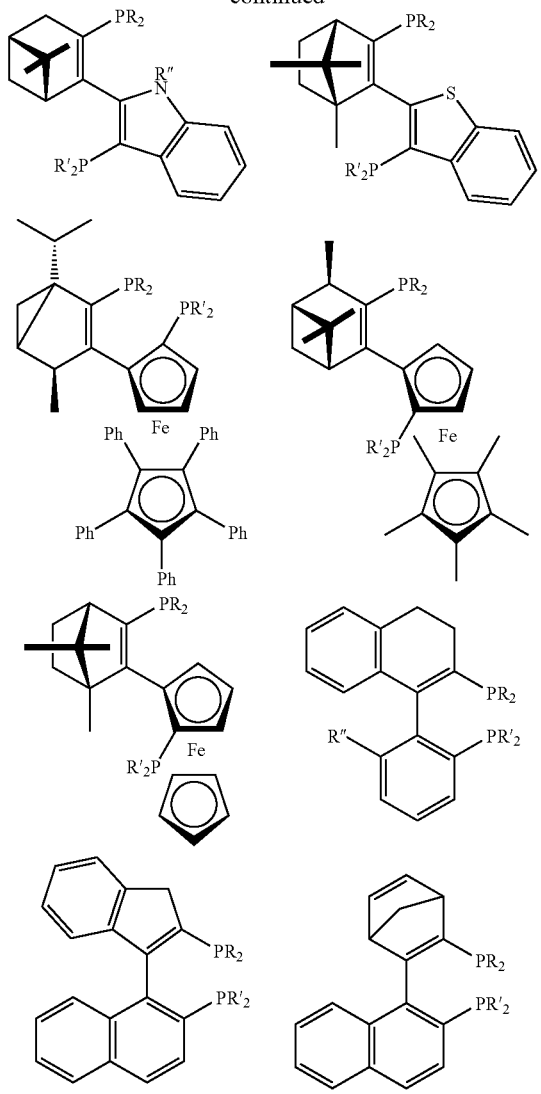

-continued

In preferred embodiments, the subject ligands are represented by general structure (Ib)

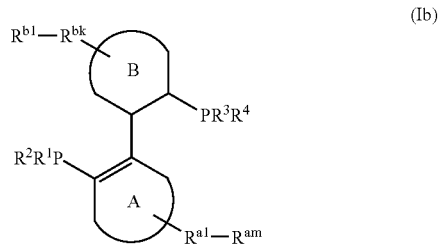

(Ib)

wherein A and B and residues $R^1$-$R^4$, $R^{a1}$-$R^{am}$ and $R^{b1}$-$R^{bk}$ remain the same as mentioned above.

Preferred embodiments are those mentioned for formulas (I) or (Ia), respectively, if being adaptable to (Ib).

In particularly preferred embodiments, the ligands are represented by general structure (Ib), and the associated definitions, wherein $R^1$, $R^2$, $R^3$ and $R^4$ for each occurrence, independently represent alkyl, alkenyl, alkynyl, alkoxyl, aryloxy, amino, alkylthio, arylthio, heteroalkyl and/or unsubstituted or substituted cyclic moiety, selected from a group consisting of monocyclic or polycyclic saturated or partially saturated carbocyclic or heterocyclic, aromatic or heteroaromatic rings said rings comprising from 4 to 8 atoms in a ring structure and said ring may bear additional substituents or be unsubstituted;

$R^1$ and $R^2$, and/or $R^3$ and $R^4$, taken together may represent a ring selected from a group consisting of monocyclic or polycyclic saturated or partially saturated carbocyclic or heterocyclic, aromatic or heteroaromatic rings said rings comprising from 3 to 8 atoms in the backbone and said ring may bear additional substituents or be unsubstituted; and the ligand, when chiral, may be provided in the form of a mixture of enantiomers or as a single enantiomer.

Particularly preferred ligands, without limitation, are depicted in FIG. 2.

FIG. 2:

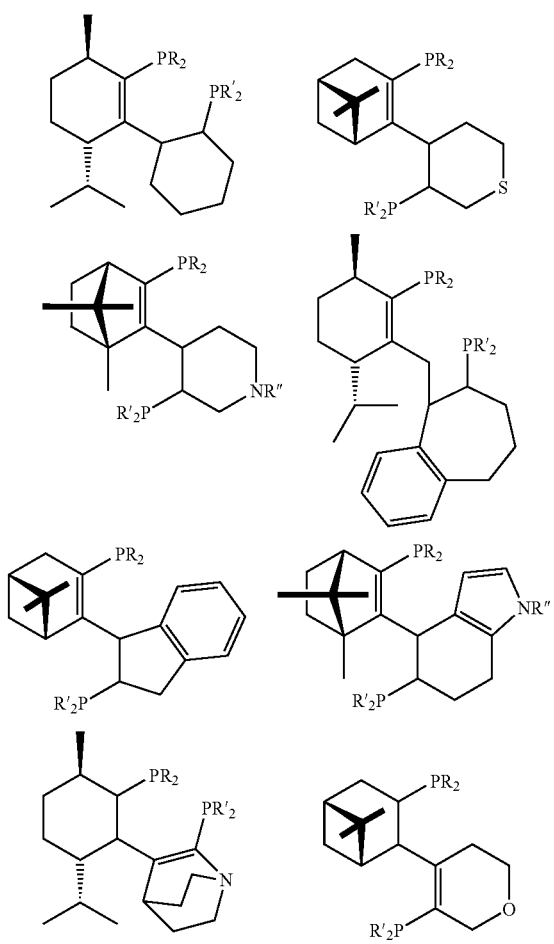

-continued

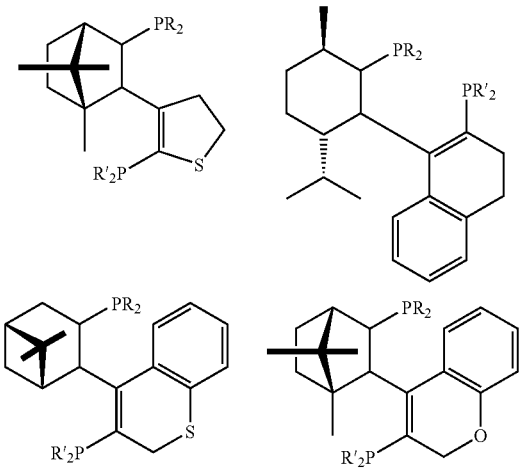

In preferred embodiments, the subject ligands are represented by general structure (Ic)

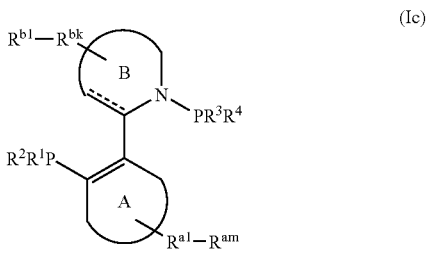

wherein A and B and residues $R^1$-$R^4$, $R^{a1}$-$R^{am}$ and $R^{b1}$-$R^{bk}$ remain the same as mentioned above.

Preferred embodiments are those mentioned for formulas (I), (Ia) or (Ib), respectively, if being adaptable to (Ic).

In particularly preferred embodiments, the ligands are represented by general structure (Ic) and the associated definitions, wherein $R^1$, $R^2$, $R^3$ and $R^4$ for each occurrence, independently represent alkyl, alkenyl, alkynyl, alkoxyl, aryloxy, amino, alkylthio, arylthio, heteroalkyl and/or unsubstituted or substituted cyclic moiety, selected from a group consisting of monocyclic or polycyclic saturated or partially saturated carbocyclic or heterocyclic, aromatic or heteroaromatic rings said rings comprising from 4 to 8 atoms in a ring structure and said ring may bear additional substituents or be unsubstituted;

$R^1$ and $R^2$, and/or $R^3$ and $R^4$, taken together may represent a ring selected from a group consisting of monocyclic or polycyclic saturated or partially saturated carbocyclic or heterocyclic, aromatic or heteroaromatic rings said rings comprising from 3 to 8 atoms in the backbone and said ring may bear additional substituents or be unsubstituted;

and the ligand, when chiral, may be provided in the form of a mixture of enantiomers or as a single enantiomer.

Particularly preferred ligands, without limitation, are depicted in FIG. 3.

FIG. 3:

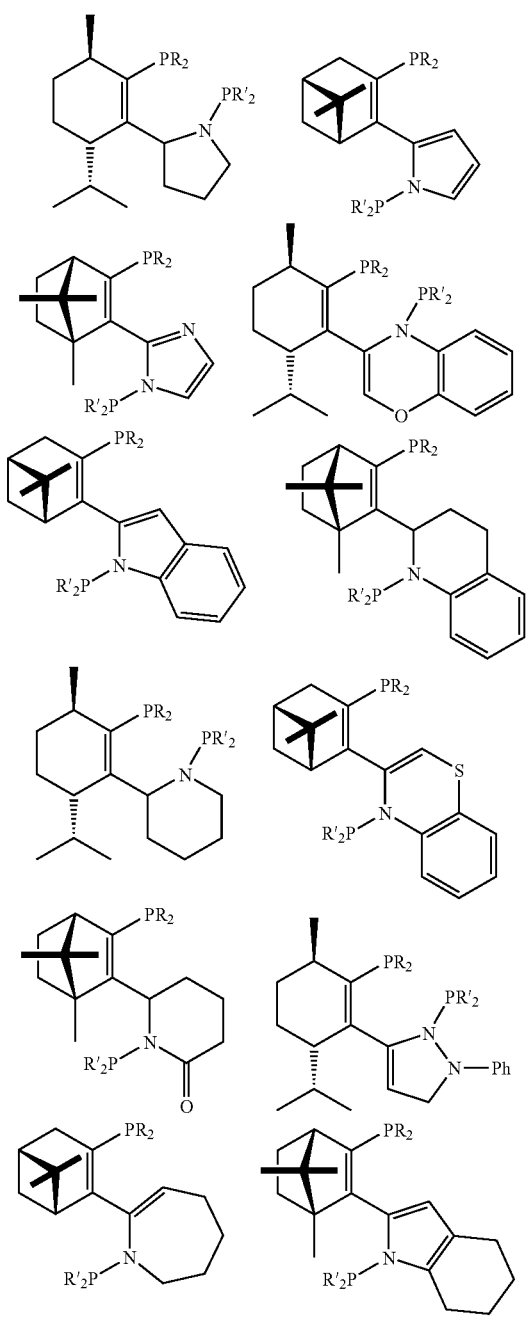

Various methods of synthesizing compounds of the general structures (I) to (Id) are available to the skilled worker. The choice of an appropriate method of preparation is mostly dependent on the availability of the corresponding starting materials and on the desired substitution pattern. Examples of synthetic methods suitable for this purposes are described below with the aid of simple examples. The processes illustrate the variety of the ligand systems obtainable by these methods. A particularly advantageous aspect of the processes of the invention is that many ligand systems can be obtained in a simple fashion in a few reaction steps.

A further embodiment of the invention is concerned with a process for preparation of ligands of the invention comprising:

in view of Y being =C or CR and Z being C or N:

coupling an organometallic reagent of general structure (II)

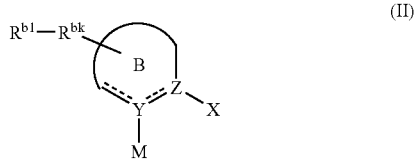

(II)

wherein

X is a halogen or hydrogen, when Z is carbon atom and X is a protective group, when Z is nitrogen and M is the group selected from alkali metal (Li, Na, K), magnesium, zinc, boronate and trialkyltin (—Sn[alkyl]3), with a derivative of general structure (III)

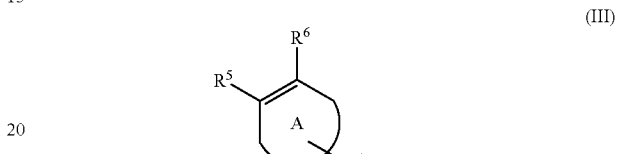

(III)

wherein $R^5$ is a halogen and $R^6$ is a leaving group selected from the group consisting of sulfonates, phosphates and carbamates in the presence of a catalyst, and subsequently introducing the phosphine groups.

The free valences of the coordinated metal (M in structure (II)) are occupied by ligands (halogen, alkoxy, solvents etc.) known to the one in the art.

More preferably, Z is magnesium, $R^5$ is a bromine and $R^6$ is a triflate;

Alternatively, in view of M being alkali metal (Li, Na, K) or magnesium:

addition of an organometallic reagent of general formula (II) to a compound of general formula (V)

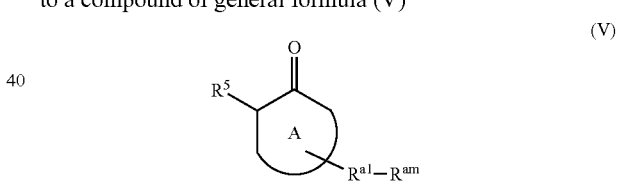

(V)

and subsequently introducing the phosphine groups;

in view of Y being N or NH, and Z being C or N:

condensing a compound of general formula (IV)

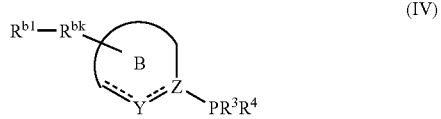

(IV)

with a compound of general formula (Va)

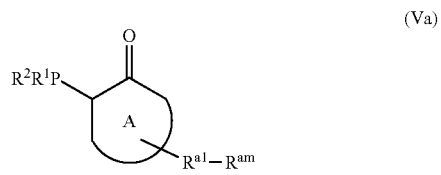

(Va)

said compound's (II-V and Va) residues and A and B being those mentioned supra.

A further embodiment of the invention is concerned with a next process for preparation of ligands of the invention comprising reacting a compound of formula (VI)

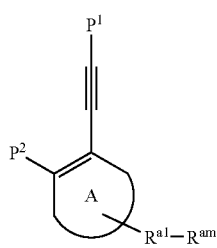

wherein

P¹ and P¹ are residues selected from (thio)phosphoryl and phosphonium cation, with a diene, and subsequent reduction to trivalent phosphorus atom, wherein A and said compound's residues being those mentioned above.

Diene in this instance mean a compound being able to react with the alkyn-part of the compound of formula (VI) in a pericyclic mode of action. Particularly preferred dienes can be depicted from subsequent list:

1,3-butadiene, 2,3-diemethyl-1,3-butadiene, 1-methoxy-3-trimethylsilyloxy-1,3-butadiene (Danishefsky-dien), 1-phenyl-3-trimethylsilyloxy-2-azapenta-1,3-diene, cyclopentadiene, 1,3-cyclohexadiene, isobenzofuran, 1,3-diphenylisobenzofuran, antracene 1,1'-dicyclopentenyl, 1,1'-dicyclohexenyl, 2,2',5,5'-tetrahydro-3,3'-bifuran and the like.

Preferably ligands of the invention can be obtained according to subsequently mentioned synthetic routes.

Synthetic Route A:

The basic olefinic-aromatic frameworks are preferably prepared by means of cross-coupling reactions of cyclic vinyl triflates with organozinc or Grignard reagents or organostannanes. Vinyl triflates are easily obtainable from the corresponding carbonyl compounds by trapping the enolate with triflating agent (K. Ritter *Synthesis* 1993, 735-762). The following commercially available or readily obtainable carbonyl compounds are particularly suitable for the preparation of the preferred ligand systems:

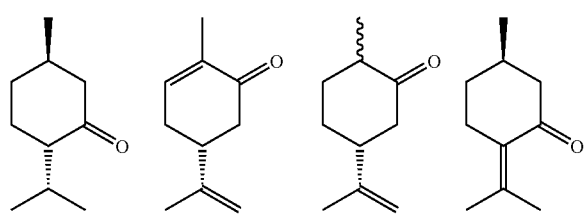

-continued

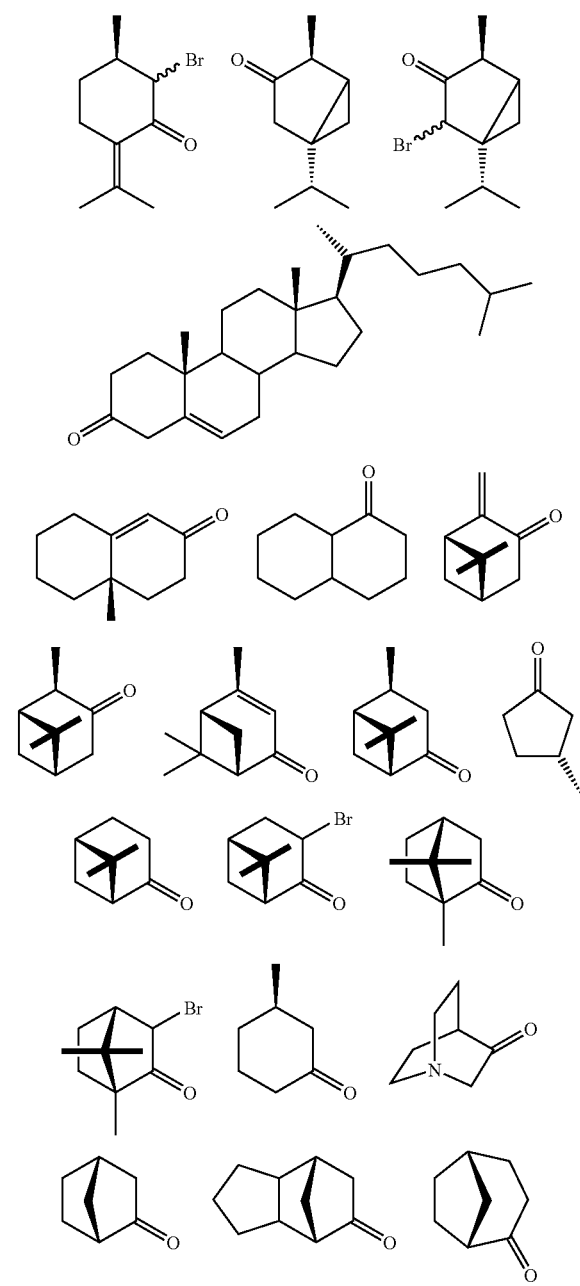

The synthesis of the basic aliphatic-aromatic frameworks can be preferably achieved by means of Kumada cross-coupling of cyclic vinyl triflates and Grignard reagents derived from haloaromatics at particularly mild conditions:

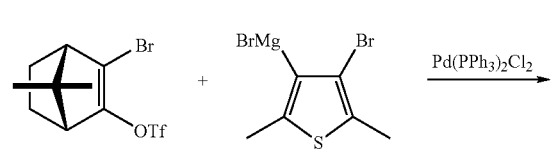

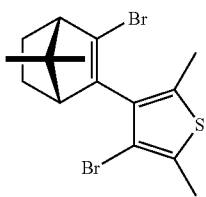

In some cases, desired frameworks can be prepared using Grignard-reagents generated from metallated hetero-aromatic compounds (see for examples L. Brandsma and H. D. Verkruijsse *Preparative Polar Organometallic Chemistry*, Vol. 1, Springer-Verlag, Berlin Heidelberg N.Y., 1987)

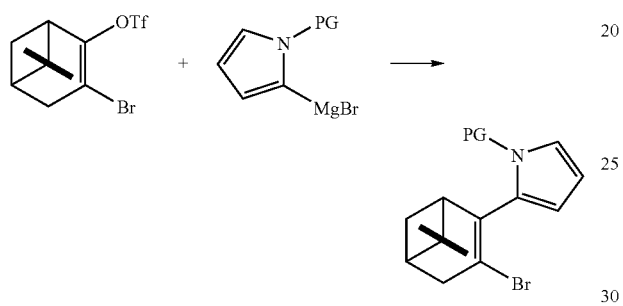

The desired precursors for the ligands of the invention can be synthesized in a simple manner via addition of the Grignard-reagents or organolithium reagents to cyclic ketones and subsequent dehydration of the intermediary tertiary alcohol under acidic conditions.

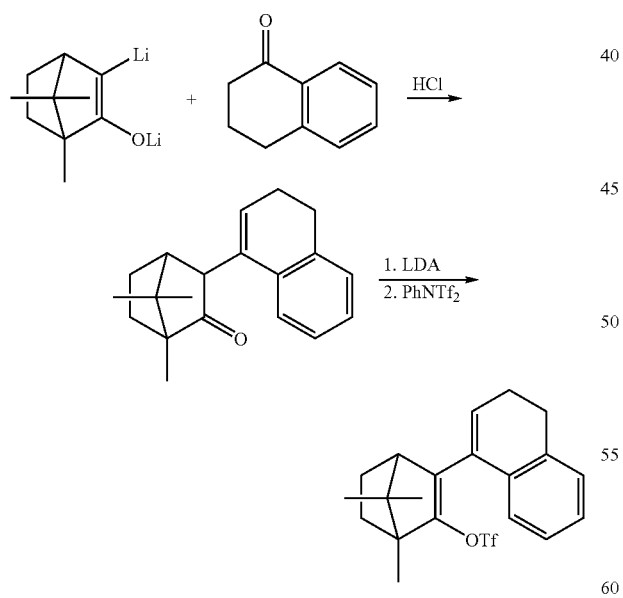

The α-keto dianions for this purpose can be prepared from the lithium enolates of α-bromo ketones (C. J. Kowalski, M. L. O'Dowd, M. K. Burke, K. W. Fields *J. Am. Chem. Soc.* 1980, 102, 5411-5412). Following triflating yields the building block suitable for the preparation of the desired ligand systems.

Synthetic Route B:

As an alternative, the basic frameworks to be used for the purposes of the invention can also be prepared by α-arylation of carbonyl compound in presence of palladium catalyst (see for review D. A. Culkin, J. F. Hartwig *Acc. Chem. Res.* 2003, 36, 234-245).

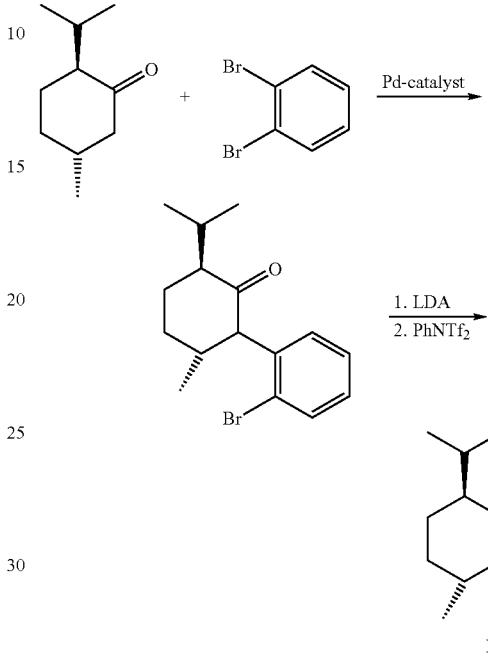

Subsequent transformation into the corresponding triflate enables the product to be converted to phosphine.

Synthetic Route C:

The diphosphine oxydes which serve the basic frameworks for the ligands of the invention can be prepared by cycloaddition of the diphosphinylated arylacetylenes to dienes. The starting diphosphines are readily obtainable, for example, by direct dimetalation of phenylacetylene at the acetylenic as well as the ortho position (P. A. A. Klusner, J. C. Hanekamp, L. Brandsma, P.v.R. Schleyer *J. Org. Chem.* 1990, 55, 1311-1321), subsequent reaction with chlorodiarylphosphines and an oxidative work-up. The resolution of the racemic adducts provides a rapid route to chiral diphosphines.

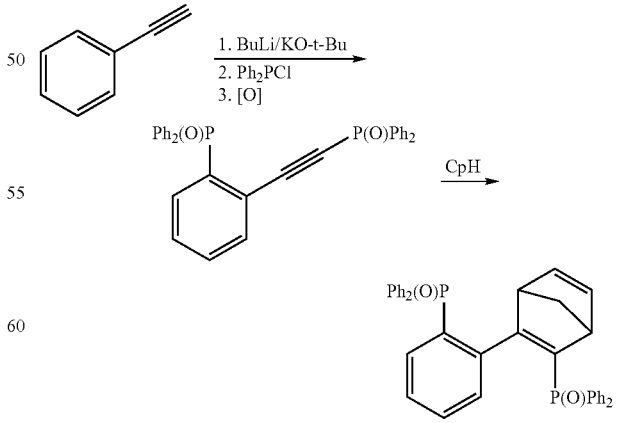

The introduction of the phosphine unit into the basic frameworks of the invention can be achieved by variations of methods known from the literature.

The introduction of the phosphine group into the olefinic or aromatic system can be successfully achieved by bromine/lithium exchange using strong bases (e.g. butyllithium) and subsequent reaction with a chlorophosphine.

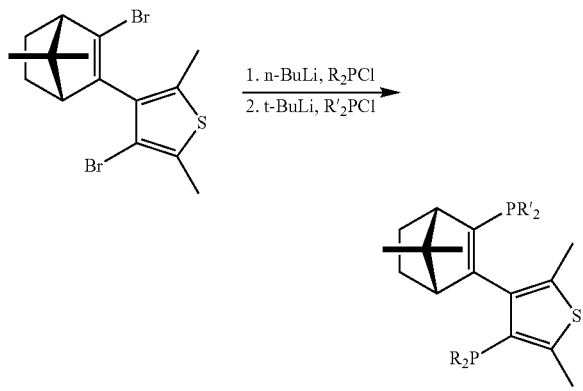

There are several methods for transformation of the vinyl triflates into tertiary phosphines or phosphine oxides. Corresponding phosphines according to the invention can be obtained from the vinyl triflates in a single step using palladium-catalyzed coupling with secondary phosphines (S. R. Gilbertson, Z. Fu, G. W. Starkey. *Tetrahedron Lett.* 1999, 40, 8509-8512).

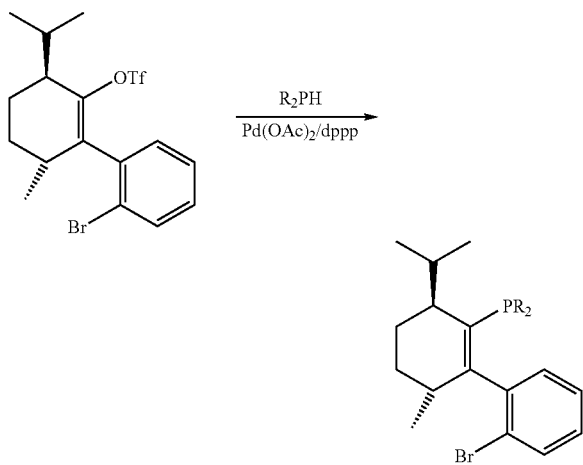

The introduction of a phosphine unit into the aliphatic system can be achieved in a single-vessel process by asymmetric hydroboration using a chiral borane in a modification of the general literature method (H. C. Brown et al. *J. Org. Chem.* 1982, 47, 5074). Subsequent transmetallation has been found to be advantageous for preparing the compounds of the invention. In one process according to the invention, the chiral borane can be transmetallated by means of diorganozinc compounds without racemization (Micouin, L.; Oestreich, M.; Knochel, P., *Angew. Chem., Int. Ed. Engl.* 1997, 36, 245-246; A. Boudier, P. Knochel, *Tetrahedron Lett.* 1999, 40, 687-690) and subsequently be phosphinated with retention of the configuration. On the other hand the phosphino or phosphinoxy group can be prepared in a simple manner by radical induced addition of secondary phosphines or phosphinoxydes to the double bond.

The ligands of the invitation prepared as oxydes or phosphonium salts can be easily reduced to free phosphines using the methods known from the literature.

The phosphine formed can, in the process of the invention, advantageously be isolated as a borane adduct and can subsequently be converted back into the free phosphine in a known manner.

A further embodiment of the present invention features a transition metal complex selected from the set of groups 5-12 metals, wherein said transition metal complex has as a ligand the compound which is defined above as ligand.

The complexes of the invention contain at least one metal atom or ion, preferably a transition metal atom or ion, in particular an atom or ion of palladium, platinum, rhodium, ruthenium, osmium, iridium, cobalt, nickel or/and copper.

The preparation of these metal-ligand complexes can be carried out in situ by reaction of a metal salt or an appropriate precursor complex with the ligands of the formula (I)-(Id). A metal-ligand complex can also be obtained by reaction of a metal salt or an appropriate precursor complex with the ligands of the formula (I)-(Id) and subsequent isolation.

Examples of metal salts are metal chlorides, bromides, iodides, cyanides, nitrates, acetates, acetyl-acetonates, hexafluoroacetylacetonates, tetrafluoro-borates, perfluoroacetates or triflates, in particular of palladium, platinium, rhodium, ruthenium, osmium, iridium, cobalt, nickel or/and copper.

Examples of precursor complexes are:

Cyclooctadienepalladium chloride, cyclooctadiene-palladium iodide, 1,5-hexadienepalladium chloride, 1,5-hexadienepalladium iodide, bis(dibenzylideneacetone)-palladium, bis(acetonitrile)palladium(II) chloride, bis(acetonitrile)palladium(II) bromide, bis(benzo-nitrile)palladium(II) chloride, bis(benzonitrile)-palladium(II) bromide, bis(benzonitrile) palladium(II) iodide, bis(allyl)palladium, bis(methallyl)palladium, allylpalladium chloride dimer, methallylpalladium chloride dimer, tetramethylethylenediaminepalladium dichloride, tetramethylethylenediaminepalladium dibromide, tetramethylethylenediaminepalladium diiodide, tetramethylethylenediaminedimethylpalladium, cyclooctadieneplatinum chloride, cyclooctadieneplatinum iodide, 1,5-hexadieneplatinum chloride, 1,5-hexadieneplatinum iodide, bis(cyclooctadiene)platinum, potassium ethylenetrichloroplatinate, cyclooctadienerhodium(I) chloride dimer, norbornadienerhodium(I) chloride dimer, 1,5-hexadienerhodium(I) chloride dimer, tris(triphenylphosphine)rhodium(I) chloride, hydridocarbonyltris-(triphenylphosphine)rhodium(I) chloride, bis(cycloocta-diene)rhodium(I) perchlorate, bis(cyclooctadiene)-rhodium(I) tetrafluoroborate, bis(cyclooctadiene)-rhodium(I) triflate, bis(acetonitrile) (cyclooctadiene)-rhodium(I) perchlorate, bis(acetonitrile) (cyclo-octadiene) rhodium(I) tetrafluoroborate, bis(aceto-nitrile) (cyclooctadiene)rhodium(I) triflate, cyclopentadienerhodium(III) chloride dimer, pentamethylcyclopentadienerhodium(III) chloride dimer, (cyclooctadiene)Ru([eta]-allyl)2, ((cyclooctadiene)Ru)2 tetraacetate, ((cyclooctadiene)Ru)2 tetra(trifluoroacetate), (arene)RuCl2 dimer, tris(triphenylphosphine)-ruthenium(II) chloride, cyclooctadieneruthenium(II) chloride, (arene)OsCl2 dimer, cyclooctadieneiridium(I) chloride dimer, bis(cyclooctene) iridium(I) chloride dimer, bis(cyclooctadiene)nickel, (cyclododecatriene)-nickel, tris(norbornene)nickel, nickel tetracarbonyl, nickel(II) acetylacetonate, (arene)copper triflate, (arene)copper perchlorate, (arene)copper trifluoro-acetate, cobalt octacarbonyl.

A final embodiment of the present invention is directed to the use of above referenced transition metal complexes.

All these complexes of the invention are particularly useful in the metal catalyzed reactions. Preferably, said reaction is selected from the group consisting of hydrogenation, hydride transfer, allylic alkylation, hydrosilylation, hydroboration, hydrovinylation, hydrocyanation, hydroformylation, olefin metathesis, hydrocarboxylation, cyclopropanation, Diels-Alder reaction, Heck reaction, isomerization, Aldol reaction, Michael addition, epoxidation, reductive amination.

A further extraordinarily advantageous use of the complexes of the invention is said hydrogenation being an asymmetric reaction. In a preferred mode the transition metal catalysts of the invention are applied in the asymmetric hydrogenation of C=C, C=O or C=N bonds, in which they display high activities and selectivities, and in asymmetric hydroformylation reaction. Here, it is found to be particularly advantageous that the ligands of the formula (I)-(Id) can be modified by simple means in a wide variety of ways so as to match them sterically and electronically to the respective substrate and the catalytic reaction.

In certain embodiments, the ligands and methods of the present invention catalyze the aforementioned transformations utilizing less than 5 mol % of the catalyst complex relative to the limiting reagent, in certain preferred embodiments less than 1 mol % of the catalyst complex relative to the limiting reagent, and in additional preferred embodiments less than 0.1 mol % of the catalyst complex relative to the limiting reagent.

The reactions of the present invention may be performed under a wide range of conditions, though it will be understood that the solvents and temperature ranges recited herein are not limitative and only correspond to a preferred mode of the process of the invention. In general, it will be desirable that reactions are run using mild conditions which will not adversely affect the reactants, the catalyst, or the product. For example, the reaction temperature influences the speed of the reaction, as well as the stability of the reactants and catalyst. The reactions will usually be run at temperatures in the range of 0° C. to 300° C., more preferably in the range 15° C. to 150° C. In preferred embodiments, the ligands and methods of the present invention catalyze the aforementioned transformations at temperatures below 50° C., and in certain embodiments they occur at room temperature.

In general, the subject reactions are carried out in a liquid reaction medium. The reactions may be run without addition of solvent. Alternatively, the reactions may be run in an inert solvent, preferably one in which the reaction ingredients, including the catalyst, are substantially soluble. Suitable solvents include ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, xylene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents.

The invention also contemplates reaction in a biphasic mixture of solvents, in an emulsion or suspension, or reaction in a lipid vesicle or bilayer. In certain embodiments, it may be preferred to perform the catalyzed reactions in the solid phase with one of the reactants anchored to a solid support.

In certain embodiments it is preferable to perform the reactions under an inert atmosphere of a gas such as nitrogen or argon.

The reaction processes of the present invention can be conducted in continuous, semi-continuous or batch fashion and may involve a liquid recycle operation as desired. The processes of this invention are preferably conducted in batch fashion. Likewise, the manner or order of addition of the reaction ingredients, catalyst and solvent are also not generally critical to the success of the reaction, and may be accomplished in any conventional fashion. In a order of events that, in some cases, can lead to an enhancement of the reaction rate or selectivity, the additive to be added to the reaction mixture.

The reaction can be conducted in a single reaction zone or in a plurality of reaction zones, in series or in parallel or it may be conducted batch wise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired-molar ratio of the starting materials. The reaction steps may be effected by the incremental addition of one of the starting materials to the other. Also, the reaction steps can be combined by the joint addition of the starting materials to the metal catalyst. When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, the ligands and catalysts of the present invention can be immobilized or polymer enlarged by adsorption, linkage or incorporation to homogeneously soluble or heterogeneous matrices. Such matrices for example, are organic polymers or SiO2-compounds. Preferably the derivatization can be achieved via one or more of substituents of the (hetero) aryl group of the basic structure. Various methods of immobilization of a homogeneous catalysts are available to the skilled worker (Chiral Catalyst Immobilization and Recycling Ed.: D. E. De Vos (, I. F. J. Vankelecom, P. A. Jacobs, VCH-Wiley, Weinheim, 2000; Reetz et al., Angew. Chem. 1997, 109, 1559; Seebach et al., Helv. Chim Acta 1996, 79, 1710; Kragl et al., Angew. Chem. 1996, 108, 684; Schurig et al., Chem. Ber./Recueil 1997, 130, 879; Bolm et al., Angew. Chem. 1997, 109, 773; Bolm et al. Eur. J. Org. Chem. 1998, 21; Salvadori et al., Tetrahedron: Asymmetry 1998, 9, 1479; Wandrey et al., Tetrahedron: Asymmetry 1997, 8, 1529; Togni et al. J. Am. Chem. Soc. 1998, 120, 10274, Salvadori et al., Tetrahedron Lett. 1996, 37, 3375; Janda et al., J. Am. Chem. Soc. 1998, 120, 9481; Andersson et al., Chem. Commun. 1996, 1135; Janda et al., Soluble Polymers 1999, 1, 1; Janda et al., Chem. Rev. 1997, 97, 489; Geckler et al., Adv. Polym. Sci. 1995, 121, 31; White et al., in "The Chemistry of Organic Silicon Conpounds" Wiley, Chichester, 1989, 1289; Schuberth et al., Macromol. Rapid Commun. 1998, 19, 309; Sharma et al., Synthesis 1997, 1217). In terms of making polymer enlarged homogeneously soluble catalysts explicit reference is made to US20020062004 and U.S. Pat. No. 6,617,480.

The ligands of the present invention and the methods based thereon can be used to produce synthetic intermediates that, after being subjected to additional methods known in the art, are transformed to desired end products, e.g., lead compounds in medicinal chemistry programs, pharmaceuticals, insecticides, antivirals and antifungals. Furthermore, the ligands of the present invention and the methods based thereon may be used to increase the efficiency of and/or shorten established routes to desired end products, e.g., lead compounds in medicinal chemistry programs, pharmaceuticals, insecticides, antivirals and antifungals.

EXAMPLES

The invention may be understood with reference to the following examples, which are presented for illustrative purposes only and which are non-limiting.

(1R)-3-bromo-2-trifluoromethylsulfoxy-1,7,7-trimethyl-bicyclo[2.2.1]heptene-2

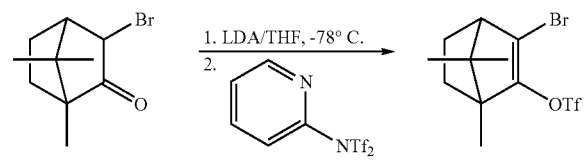

To the solution of (1R)-3-bromocamphor (46.22 g; 0.2 mol) in 230 ml THF 2M LDA solution (105 ml, 0.21 mol) was added drop wise at −78° C. After 30 min stirring at the same temperature a solution of 2-[N,N-bis(trifluoromethane sulfonyl)amino]pyridine (75.23 g; 0.21 mol) in 80 ml of THF was added drop wise and then allowed to warm to room temperature over night. Then reaction mixture was cooled in ice bath and 250 ml of ice cold water was carefully added and product was extracted with ether (8×50 ml). The combined organic layers were washed with ice cold 2N NaOH, followed with brine, and dried over $MgSO_4/K_2CO_3$. The residue after concentration on rotary evaporator was dissolved in 200 ml of hexane and filtered trough a shot pad of basic Al2O3. Filtrate was concentrated on rotary evaporator and the resulting oil was distilled in vacuum to give 64 g (88%) of product as colorless oil (b.p. 73-76° C./0.5 mbar).

$^1$H NMR (CDCl$_3$) δ=0.74 (s, 3H), 0.93 (s, 3H), 1.03 (s, 3H), 1.23 (ddd, J=12.6, J=9.2, J=3.7, 1H), 1.43 (ddd, J=12.4, J=8.9, J=3.4, 1H), 1.62 (ddd, J=12.4, J=8.5 J=3.9, 1H), 1.87 (ddt, J=12.5, J=8.6, J=3.7, 1H), 2.46 (d, J=3.7, 1H); $^{13}$C NMR (CDCl$_3$) δ=9.95, 18.71, 19.36, 24.96, 32.05, 56.16, 56.87, 58.72, 113.28, 118.43 (q, J=320.3), 151.99.

(1R)-3-bromo-(4-bromo-2,5-dimethylthienyl-3)-1,7,7-trimethylbicyclo[2.2.1]heptene-2

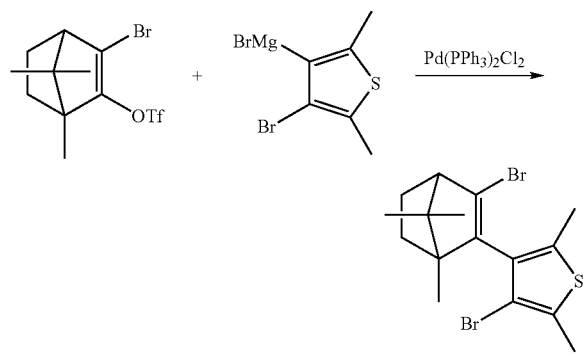

Grignard solution (prepared from 3,4-dibromo-1,5-dimethylthiophene (77.31 g, 0.286 mol) and magnesium (7.29 g, 0.3 mol) in 250 ml THF) was transferred in the 500 ml flask containing Pd(PPh$_3$)$_2$Cl$_2$ (5 g, 7 mmol) and 3-bromo-2-trifluoromethanesulfoxybornylene (52 g, 0.143 mol) and resulted reaction mixture was stirred at 50° C. under argon over night. CO$_2$ was passed trough reaction mixture keeping the exothermic reaction under control by occasional cooling. After temperature was slow down 200 ml of aqueous NH$_4$Cl were added with vigorously stirring, aqueous layer extracted three times with ether, combined org. layers were washed with brine, dried over MgSO$_4$, solvent evaporated in vacuum, the residue dissolved in 200 ml hexane and filtered trough silica gel pad. After evaporation of hexane resulting oil was fractionated in vacuum to give 45.36 g (78%) of product as colorless viscous oil (b.p.=126-139° C./0.001 mbar)

$^1$H NMR (C$_6$D$_6$) δ=0.61 (s, 3H), 0.84 (s, 3H), 1.01 (s, 3H), 1.48 (ddd, J=12.2, J=8.5, J=3.8, 1H), 1.55 (ddd, J=12.3, J=8.9, J=3.6, 1H), 1.76 (ddt, J=12.0, J=8.5, J=3.6, 1H), 2.06 (s, 3H), 2.08-2.12 (m, 1H), 2.14 (s, 3H), 2.46 (d, J=4.0, 1H); $^{13}$C NMR (C$_6$D$_6$) δ=12.44, 15.16, 15.28, 19.57, 19.80, 24.93, 32.78, 57.65, 59.86, 61.01, 111.13, 128.10, 130.98, 132.75, 134.84, 140.90.

(1R)-3-bromo-(4-diphenylphosphino-2,5-dimethylthienyl-3)-1,7,7-trimethylbicyclo[2.2.1]heptene-2

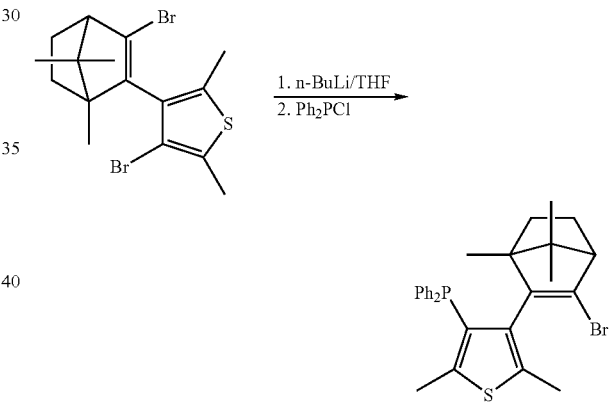

To a cooled to −78° C. solution of 3-bromo-(4-bromo-2,5-dimethylthienyl-3)bornylene (4.04 g, 10 mmol) in 50 ml THF under argon was added drop wise 1.6 M hexane solution of n-butyllithium (7.5 ml, 12 mmol) maintaining the internal temperature between −60 and −78° C. The resulting solution was stirred at −78° C. for 30 min after which chlorodiphenylphosphine (2.64 g, 12 mmol) was added. The mixture was allowed to warm to room temperature and quenched by careful addition of aq. NH$_4$Cl (30 ml). The upper layer separated and the aqueous layer was extracted with 20 ml ether. The combined organic layers were dried over MgSO$_4$, and concentrated in vacuum to give viscous oil which solidified by stirring with 20 ml of chilled methanol, precipitate was filtered off, washed with minimal amounts of cold methanol, then with minimal amounts of cold hexane and dried in vacuum to give 3.75 g (74%) of product as colorless solid.

$^1$H NMR (CDCl$_3$) δ=0.81 (s, 3H), 0.86 (s, 3H), 1.15 (s, 3H), 1.34 (ddd, J=12.0, J=8.5, J=3.6, 1H), 1.52 (ddd, J=12.0, J=8.9, J=3.4, 1H), 1.63 (dddd, J=11.9, J=8.9, J=5.4, J=3.2, 1H), 1.71 (s, 3H), 1.80 (ddd, J=11.8, J=8.4, J=3.5, 1H), 2.38 (s, 3H), 2.49 (d, J=3.7, 1H), 7.19-7.40 (m, 10H); $^{13}$C NMR (CDCl$_3$) δ=12.56, 14.64 (J=1.8), 16.41, 19.84, 19.95, 24.50, 32.46 (J=12.1), 57.59 (J=2.4), 59.39, 60.57, 126.88 (J=1.8), 127.23, 127.66, 128.12 (J=5.4), 128.49 (J=5.4), 129.66 (J=16.3), 131.43 (J=17.6), 131.97 (J=18.2), 133.65 (J=8.5), 136.43 (J=12.7), 137.80 (J=14.5), 138.80 (J=44.2), 141.99, 144.39 (j=9.1); $^{31}$P NMR (CDCl$_3$) δ=−20.86.

(1R)-3-diphenylphosphino-(4-diphenylphosphino-2,5-dimethylthienyl-3)-1,7,7-trimethylbicyclo[2.2.1]heptene-2 (Ligand T1)

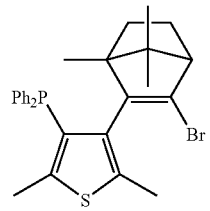

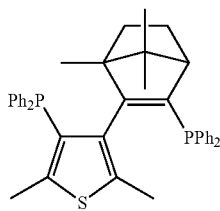

To a cooled to −90° C. solution of 3-bromo-(4-diphenylphosphino-2,5-dimethylthienyl-3)bornylene (3.06 g, 6 mmol) in 40 ml THF were added drop wise 1.7 M pentane solution of tert-butyllithium (8 ml, 14 mmol). The resulting solution was stirred for 30 min and chlorodiphenylphosphine (1.55 g, 7 mmol) was added at this temperature. The mixture was allowed to warm to ambient temperature and the reaction was quenched by careful addition of aqueous NH$_4$Cl (20 ml). The layers were separated and the organic layer was dried over MgSO$_4$, filtered and concentrated under reduced pressure. Chromatography of the residue using hexane to hexane-ethylacetate (50:1) as eluent afforded the title compound as colorless oil which is solidified by stirring with chilled methanol (15 ml). Yield 1.8 g (49%).

$^1$H NMR (CDCl$_3$) δ=0.73 (s, 3H), 0.76 (d, J=1.2, 3H), 0.94 (s, 3H), 1.01 (ddd, J=11.6, J=8.8, J=3.7, 1H), 1.27 (ddd, J=12.0, J=8.4, J=3.8, 1H), 1.54-1.68 (m, 2H), 1.71 (s, 0.3H), 2.23 (s, 3H), 2.57 (dd, J=1.3, J=3.7), 7.15-7.51 (m, 20H); $^{31}$P NMR (CDCl$_3$) δ=−23.8 (d, J=24.3), −22.4 (d, J=24.3), (1R)-3-di-(3,5-dimethylphenyl)phosphino-(4-diphenylphosphino-2,5-dimethylthienyl-3)-1,7,7-trimethylbicyclo[2.2.1]heptene-2 (Ligand T2)

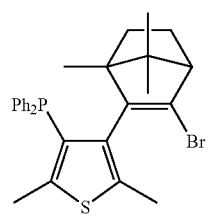

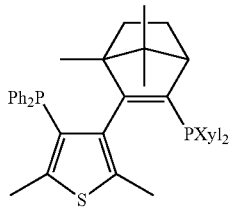

To a cooled to −90° C. solution of 3-bromo-(4-diphenylphosphino-2,5-dimethylthienyl-3)bornylene (3.06 g, 6 mmol) in 40 ml THF were added drop wise 1.7 M pentane solution of tert-butyllithium (8 ml, 14 mmol). The resulting solution was stirred for 30 min and bis-(3,5-dimethylphenyl)chlorophosphine (1.94 g, 7 mmol) was added at this temperature. The mixture was allowed to warm to room temperature and the reaction was quenched by careful addition of aqueous NH$_4$Cl (20 ml). The layers were separated and the organic layer was dried over MgSO$_4$, filtered and concentrated under reduced pressure. Chromatography of the residue using hexane-ethylacetate (50:2) as eluent afforded 2.9 g (72%) of the title compound as colorless solid. An analytical sample was found by recrystallization from hot ethanol.

$^1$H NMR (CDCl$_3$) δ=0.73 (s, 3H), 0.74 (d, J=1.0, 3H), 0.95 (s, 3H), 1.02 (ddd, J=11.8, J=8.8, J=3.8, 1H), 1.26 (ddd, J=12.2, J=8.6, J=3.7, 1H), 1.54-1.68 (m, 2H), 1.73 (s, 3H), 2.13 (s, 6H), 2.23 (s, 3H), 2.27 (s, 6H), 2.58 (dd, J=1.3, J=3.7), 6.82 (s, 1H), 6.91 (s, 1H), 7.08 (d, J=7.7, 2H), 7.11 (d, J=7.5, 2H), 7.16-7.49 (m, 10H); $^{31}$P NMR (CDCl$_3$) δ=−23.7 (d, J=23.6), −22.3 (d, J=23.6).

(1R)-3-bromo-[4-di(3,5-dimethylphenyl)phosphino-2,5-dimethylthienyl-3]-1,7,7-trimethylbicyclo[2.2.1]heptene-2

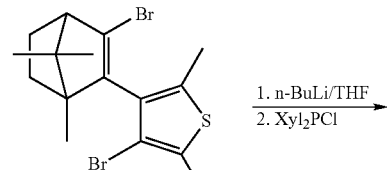

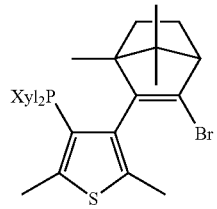

To a cooled to −78° C. solution of 3-bromo-(4-bromo-2,5-dimethylthienyl-3)bornylene (8.08 g, 20 mmol) in 60 ml THF under argon was added drop wise 1.6 M hexane solution of n-butyllithium (15.6 ml, 25 mmol) maintaining the internal temperature between −60 and −78° C. The resulting solution was stirred at −78° C. for 30 min after which bis-(3,5-dimethylphenyl)chlorophosphine (6.92 g, 25 mmol) was added. The mixture was allowed to warm to room temperature and quenched by careful addition of aq. NH$_4$Cl (30 ml). The upper layer separated and the aqueous layer was extracted with 20 ml ether. The combined organic layers were dried over MgSO₄, and concentrated in vacuum to give viscous oil which solidified by stirring with 30 ml of chilled methanol, precipitate was filtered off, washed two times with chilled methanol and dried in vacuum to give 10.6 g (71%) of product as colorless solid.

$^1$H NMR (CDCl₃) δ=0.80 (s, 3H), 0.85 (s, 3H), 1.15 (s, 3H), 1.34 (ddd, J=12.1, J=8.5, J=3.8, 1H), 1.50 (ddd, J=11.8, J=9.0, J=3.4, 1H), 1.65-1.71 (m, 1H), 1.76 (s, 3H), 1.78-1.82 (m, 1H), 2.21 (s, 6H), 2.27 (s, 6H), 2.38 (s, 3H), 2.48 (d, J=3.7, 1H), 6.82 (s, 1H), 6.88 (d, J=7.7, 2H), 6.90 (s, 1H), 6.99 (d, J=7.4, 2H); $^{31}$P NMR (CDCl₃) δ=−20.70;

(1R)-3-diphenylphosphino-[4-di-(3,5-dimethylphenyl)phosphino-2,5-dimethylthienyl-3)-1,7,7-trimethylbicyclo[2.2.1]heptene-2 (Ligand T3)

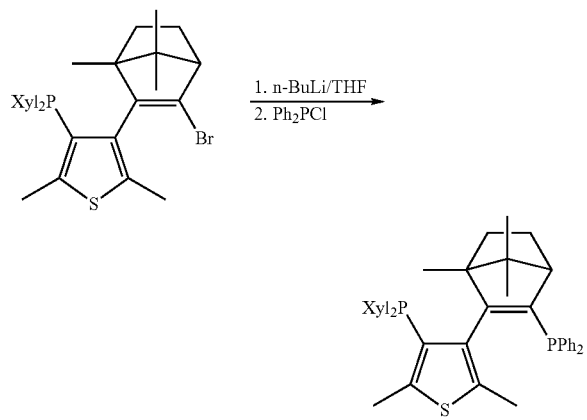

To a cooled to −90° C. solution of 3-[4-di(3,5-dimethylphenyl)phosphino-2,5-dimethylthienyl-3]bornylene (2.82 g, 5 mmol) in 35 ml THF were added drop wise 1.7 M pentane solution of tert-butyllithium (8 ml, 14 mmol). The resulting solution was stirred for 30 min and chlorodiphenylphosphine (1.77 g, 8 mmol) in 5 ml THF were added at −90° C. The mixture was allowed to warm to room temperature and quenched by careful addition of aqueous NH₄Cl (20 ml). The layers were separated and the organic layer was dried over MgSO₄, filtered and concentrated under reduced pressure. Chromatography of the residue using hexane-ethyl acetate (100:1) as eluent afforded 1.06 g (72%) of the title compound as colorless solid. An analytical sample was found by recrystallization from hot ethanol.

$^1$H NMR (CDCl₃) δ=0.72 (s, 3H), 0.76 (d, J=1.2, 3H), 0.91 (s, 3H), 1.00-1.07 (m, 1H), 1.26-1.32 (m, 1H), 1.55-1.62 (m, 1H), 1.73-1.80 (m, 1H), 1.77 (s, 3H), 2.19 (s, 6H), 2.26 (s, 3H), 2.27 (s, 6H), 2.54 (dd, J=1.3, J=3.7), 6.80-7.52 (m, 16H); $^{31}$P NMR (CDCl₃) δ=−23.2 (d, J=20.1), −22.4 (d, J=20.1).

General Procedure for Catalytic Asymmetric Hydrogenation with Rh(I) Complexes

In a glove box, the catalyst was made by mixing Rh(COD)₂BF₄ (100 μl of 0.02M solution in CH₂Cl₂, 2 μmol) and ligand (110 μl of 0.02M solution in CH₂Cl₂ 2.2 μmol) solutions in the 1.5 ml vial with stirring bar. The mixture was stirred for 15 min and substrate (0.5 ml of 0.4M solution, 0.2 mmol) solution in the appropriate solvent was added. Hydrogenation was performed at room temperature under 8 bar of hydrogen pressure for 16 h. The hydrogen was released and the reaction mixture was passed through a silica gel plug. The conversion and enantiomeric excess was determined by GC or HPLC analysis using a chiral columns without further purification.

TABLE 1

Enantioselective hydrogenation of dimethyl itaconate using Rh(I)-complexes with new ligands
([Substrate]:[Rh]:[Ligand] = 100:1:1.1) [a]

| 1. Ligand | 2. Solvent | Conversion | ee [b] |
|---|---|---|---|
| T1 | MeOH | 100 | 92 |
| T1 | CH₂Cl₂ | 100 | 83 |
| T1 | THF | 100 | 80 |
| T2 | THF | 100 | 84 |
| T3 | MeOH | 100 | 84 |
| T3 | CH₂Cl₂ | 100 | 90 |
| T3 | THF | 100 | 91 |

[a] The reaction was carried out at rt under an initial hydrogen pressure of 8 bar for 16 h. The catalyst was prepared in situ from Rh(COD)₂BF₄ and ligand.
[b] Enantiomeric excesses were determined by chiral HPLC on ChiralCel OD (Hexane:2-PrOH 95:5).

TABLE 2

Enantioselective hydrogenation of 2-(N-acetamido)styrene using Rh(I)-complexes with new ligands
([Substrate]:[Rh]:[Ligand] = 100:1:1.1) [a]

| Ligand | Solvent | Conversion | ee [b] |
|---|---|---|---|
| T1 | MeOH | 100 | 82 |
| T2 | CH₂Cl₂ | 100 | 88 |
| T2 | MeOH | 100 | 92 |

[a] The reaction was carried out at rt under an initial hydrogen pressure of 8 bar for 16 h. The catalyst was prepared in situ from Rh(COD)₂BF₄ and ligand.
[b] Enantiomeric excesses were determined by GC analysis on Chrompak chiral column (CP Chirasil-DEX CB).

TABLE 3

Enantioselective hydrogenation of (Z)-α-(N-acetamido)cinnamates using Rh(I)-complexes with new ligands ([Substrate]:[Rh]:[Ligand] = 100:1:1.1) [a]

$$\text{RO-CO-C(=CHPh)-NHAc} \xrightarrow[\text{H}_2 \text{ (8 bar), 16 h, rt}]{\text{Rh(COD)}_2\text{BF}_4 \text{ (1 mol \%)} \\ \text{Ligand (1.1 mol \%)}} \text{RO-CO-CH(CH}_2\text{Ph)-NHAc}$$

| R | Ligand | Solvent | Conversion | ee [b] |
|---|---|---|---|---|
| H | T1 | MeOH | 100 | 99 |
| H | T1 | CH$_2$Cl$_2$ | 100 | 98 |
| H | T2 | MeOH | 100 | 96 |
| H | T2 | CH$_2$Cl$_2$ | 100 | 96 |
| H | T3 | MeOH | 100 | 94 |
| H | T3 | CH$_2$Cl$_2$ | 100 | 99 |
| Me | T1 | MeOB | 100 | 98 |
| Me | T1 | CH$_2$Cl$_2$ | 100 | 99 |
| Me | T1 | THF | 100 | 98 |
| Me | T2 | MeOH | 100 | 95 |
| Me | T2 | CH$_2$Cl$_2$ | 100 | 97 |
| Me | T2 | THF | 100 | 96 |

[a] The reaction was carried out at rt under an initial hydrogen pressure of 8 bar for 16 h. The catalyst was prepared in situ from Rh(COD)$_2$BF$_4$ and ligand.
[b] Enantiomeric excesses were determined by chiral HPLC on ChiralPak AD (Hexane:2-PrOH 75:25).

TABLE 4

Enantioselective hydrogenation of methyl (E)- and (Z)-3-(N-acetamido)-2-butenoate using Rh(I)-complexes with new ligands ([Substrate (0.2 M)]:[Rh]:[Ligand] = 100:1:1.1) [a]

| Configuration | Ligand | Solvent | Conversion | ee [b] |
|---|---|---|---|---|
| 3. E | T1 | MeOH | 100 | 99 |
| E | T2 | MeOH | 100 | 99 |
| E | T3 | MeOH | 100 | 85 |
| E | T1 | CH$_2$Cl$_2$ | 100 | 99 |
| E | T2 | CH$_2$Cl$_2$ | 100 | 99 |
| E | T3 | CH$_2$Cl$_2$ | 100 | 87 |
| E | T1 | THF | 100 | 98 |
| E | T2 | THF | 100 | 98 |
| E | T3 | THF | 100 | 90 |
| Z | T2 | MeOH | 100 | 93 |
| Z | T2 | CH$_2$Cl$_2$ | 100 | 94 |

[a] The reaction was carried out at rt under an initial hydrogen pressure of 8 bar for 16 h. The catalyst was prepared in situ from Rh(COD)$_2$BF$_4$ and ligand.
[b] Enantiomeric excesses were determined by GC analysis on Chrompak chiral column. (CP Chirasil-DEX CB).

TABLE 5

Enantioselective hydrogenation of 2-Acetoxy-3-Phenyl acrylic acid, using Rh(I)-complexes with new ligands ([Substrate]:[Rh]:[Ligand] = 100:1:1.1) [a]

| Ligand | Solvent | Conversion | ee [b] |
|---|---|---|---|
| T1 | MeOH | 37 | 79 |
| T2 | MeOH | 70 | 86 |
| T2 | MeOH | 30 | 74 |

[a] The reaction was carried out at rt under an initial hydrogen pressure of 8 bar for 16 h. The catalyst was prepared in situ from Rh(COD)$_2$BF$_4$ and ligand.
[b] Enantiomeric excesses were determined by chiral HPLC on ChiralPak AD (Hexane:2-PrOH 98:2).

General Procedure for Catalytic Asymmetric Hydrogenation with Ru(II) Complexes

In a glove box, the catalyst was made by mixing [Ru(C$_6$H$_6$)Cl$_2$]$_2$ (50 µl of 0.02M solution in DMF, 1 µmol) and ligand (55 µl of 0.04M solution in CH$_2$Cl$_2$, 2.2 µmol) solutions in the 1.5 ml vial with stirring bar. The mixture was heated to 120° C. and, after being cooled to ambient temperature, substrate (0.5 ml of 0.4M solution, 0.2 mmol) solution in dichloromethane was added. Hydrogenation was performed at 60° C. under 50 bar of hydrogen pressure for 16 h. The reaction mixture was passed through a silica gel plug using hexane as eluent. The conversion and enantiomeric excess was determined by HPLC analysis using a chiral column without further purification.

TABLE 6

Enantioselective hydrogenation of ethyl 3-oxo-3-thiophen-2-yl-propionate using Ru(II)-complexes with new ligands ([Substrate]:[Ru]:[Ligand] = 100:1:1.1) [a]

| Ligand | Solvent | Conversion | ee [b] |
|---|---|---|---|
| T1 | CH$_2$Cl$_2$ | 100 | 75 |
| T2 | CH$_2$Cl$_2$ | 100 | 59 |
| T3 | CH$_2$Cl$_2$ | 100 | 57 |

[a] The reaction was carried out at 60° C. under an initial hydrogen pressure of 50 bar for 16 h. The catalyst was prepared in situ from [Ru(C$_6$H$_6$)Cl$_2$]$_2$ and ligand.
[b] Enantiomeric excesses were determined by chiral HPLC on ChiralPakAS (Hexane + 0.5% TFA:2-PrOH 90:10).

TABLE 7

Enantioselective hydrogenation of dimethyl
itaconate using Ru(II)-complexes with new ligands
([Substrate]:[Rh]:[Ligand] = 100:1:1.1) [a]

| Ligand | Solvent | Conversion | ee [b] |
|---|---|---|---|
| T1 | MeOH | 100 | 59 |
| T2 | $CH_2Cl_2$ | 100 | 83 |
| T3 | MeOH | 98 | 70 |

[a] The reaction was carried out at 60° C. under an initial hydrogen pressure of 50 bar for 16 h. The catalyst was prepared in situ from [Ru(C₆H₆)Cl₂]₂ and ligand.
[b] Enantiomeric excesses were determined by GC analysis on Chrompak chiral column (CP Chirasil-DEX CB).

General Procedure for Catalytic Asymmetric Hydrogenation with Ru(II) Diamine Complexes In a glove box, the catalyst was made by mixing [Ru(C₆H₆)Cl₂]₂ (50 μl of 0.02M solution in DMF, 2 μmol) and ligand (55 μl of 0.04M solution in $CH_2Cl_2$, 2.2 μmol) solutions in the 1.5 ml vial with stirring bar. The mixture was heated to 120° C. and, after being cooled to ambient temperature, a solution of (1S,2S)-1,2-diphenylethylenediamine (S,S-DPEN) (110 μl of 0.02M solution in $CH_2Cl_2$, 2.2 μmol) was added mixture was stirred for 2 h. t-BuOK (100 μl of 0.1M solution in 2-PrOH, 10 μmol) solution was added and the catalyst solution was stirred for 20 min before substrate (0.5 ml of 0.4M solution in 2-PrOH, 0.2 mmol) was added. Hydrogenation was performed at room temperature under 8 bar of hydrogen pressure for 16 h. The reaction mixture was passed through a silica gel plug using hexane as eluent. The conversion and enantiomeric excess was determined by HPLC analysis using a chiral column without further purification.

TABLE 8

Enantioselective hydrogenation of acetophenone
using Ru(II) complexes with new ligands and (S,S)-DPEN
([Substrate]:[Rh]:[Ligand]:[DPEN] = 100:1:1.1) [a]

| Ligand | Conversion | ee [b] |
|---|---|---|
| T1 | 98 | 79 |
| T2 | 98 | 81 |
| T3 | 98 | 91 |

[a] The reaction was performed with 0.4 M solution of acetophenone in 2-PrOH with added t-BuOK (5 mol %) at rt under an initial hydrogen pressure of 8 bar for 16 h. The catalyst was prepared in situ from Rh (COD)₂BF₄, (S,S)-DPEN and ligand.
[b] Enantiomeric excesses were determined by chiral HPLC on ChiralCel OD (Hexane:2-PrOH 90:10).

The invention claimed is:

1. A ligand or its salt of the general formula:

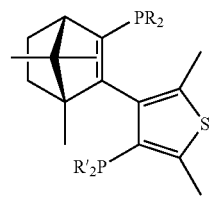

wherein R and R' are each independently: alkyl; aryl; aralkyl; alkenyl; alkynyl; alkoxyl; aryloxyl; alkylthio; arylthio; or an unsubstituted or substituted cyclic moiety wherein said cyclic moeity is a monocyclic or polycyclic saturated or partially saturated carbocyclic or heterocyclic, aromatic or heteroaromatic ring, said ring comprising 4 to 8 atoms and 0 to 3 heteroatoms;

and wherein said ligand, when chiral, may be present as either a mixture of enantiomers or as a single enantiomer.

2. The ligand of claim 1, wherein R and R' are each independently an unsubstituted or substituted cyclic moiety wherein said cyclic moeity is a monocyclic or polycyclic saturated or partially saturated carbocyclic or heterocyclic, aromatic or heteroaromatic ring, said ring comprising 4 to 8 atoms and 0 to 3 heteroatoms.

3. The ligand of claim 1, wherein R is an aromatic or heteroaromatic ring comprising 4 to 8 atoms and 0 to 3 heteroatoms.

4. The ligand of claim 1, wherein R is an aromatic ring comprising 4 to 8 atoms.

5. The ligand of claim 1, wherein R' is an aromatic or heteroaromatic ring comprising 4 to 8 atoms and 0 to 3 heteroatoms.

6. The ligand of claim 1, wherein R' is an aromatic ring comprising 4 to 8 atoms.

7. The ligand of claim 1, wherein R and R' are both aromatic rings comprising 4 to 8 atoms.

8. The ligand of claim 1, wherein R is phenyl.

9. The ligand of claim 1, wherein R' is phenyl.

10. The ligand of claim 1, wherein R and R' are both phenyl.

11. The ligand of claim 1, wherein R is dimethylphenyl.

12. The ligand of claim 11, wherein R' is phenyl.

13. The ligand of claim 1, wherein R' is dimethylphenyl.

14. The ligand of claim 13, wherein R is phenyl.

* * * * *